United States Patent

Lociuro et al.

[11] Patent Number: 6,008,225
[45] Date of Patent: Dec. 28, 1999

[54] DERIVATIVES OF ANTIBIOTIC GE2270 FACTORS $C_{2A}$, $D_2$ AND E

[75] Inventors: Sergio Lociuro, Verona; Paolo Tavecchia, Rho; Romeo Ciabatti, Novata Milanese; Ermenegildo Restelli, Gerenzano, all of Italy

[73] Assignee: BioSearch Italia, S.p.A., Italy

[21] Appl. No.: 09/101,077

[22] PCT Filed: Feb. 12, 1997

[86] PCT No.: PCT/EP97/00628

§ 371 Date: Jun. 29, 1998

§ 102(e) Date: Jun. 29, 1998

[87] PCT Pub. No.: WO97/30078

PCT Pub. Date: Aug. 21, 1997

[30] Foreign Application Priority Data

Feb. 14, 1996 [EP] European Pat. Off. .............. 96102145

[51] Int. Cl.[6] .............................. C07K 5/078; C07K 7/56; C07K 5/06; A61K 38/05
[52] U.S. Cl. .......................................... 514/279; 540/455
[58] Field of Search .............................. 540/455; 514/279

[56] References Cited

U.S. PATENT DOCUMENTS

| | | | |
|---|---|---|---|
| 5,139,778 | 8/1992 | Selva et al. | 424/117 |
| 5,202,241 | 4/1993 | Selva et al. | 435/71.3 |
| 5,514,649 | 5/1996 | Selva et al. | 514/9 |
| 5,599,791 | 2/1997 | Tavecchia et al. | 514/9 |
| 5,747,295 | 5/1998 | Selva et al. | 435/71.3 |
| 5,891,869 | 4/1999 | Lociuro et al. | 514/183 |

FOREIGN PATENT DOCUMENTS

| | | |
|---|---|---|
| WO 94/05798 | 3/1994 | WIPO . |
| WO 96/14427 | 5/1996 | WIPO . |
| WO 96/24607 | 8/1996 | WIPO . |
| WO 96/24608 | 8/1996 | WIPO . |

OTHER PUBLICATIONS

Journal of Antibiotics, vol. 47(12), pp. 1564–1567 (1994).
Journal of Antibiotics, vol. 47(10), pp. 1153–1159 (1994).

*Primary Examiner*—Mukund J. Shah
*Assistant Examiner*—Bruck Kifle
*Attorney, Agent, or Firm*—Killworth, Gottman, Hagan & Schaeff, LLP

[57] ABSTRACT

Mono- or di-substituted derivatives of GE2270 factors $C_{2a}$, $D_2$ and E of general formula (I), wherein W represents a moiety of formula (a), (b) or (c), $R^1$ and $R^2$ representing a variety of substituents, $X^1$ is methyl, $X^2$ is a —$CH_2$—$W^1$ moiety and $X^3$ is methylamino or amino, or $X^1$ is a —$CH_2$—$W^1$ moiety, $X^2$ is methoxymethylene and $X^3$ is methylamino, with the proviso that when $X^3$ is amino, then W must be 2-(aminocarbonyl)-pyrrolidinyl; with the further proviso that when W is 2-(aminocarbonyl)-pyrrolidinyl, then $W^1$ cannot be hydroxy; and the pharmaceutically acceptable salts thereof. The mono- or di-substituted derivatives of antibiotic GE 2270 of formula (I) are antimicrobial agents mainly active against gram positive bacteria.

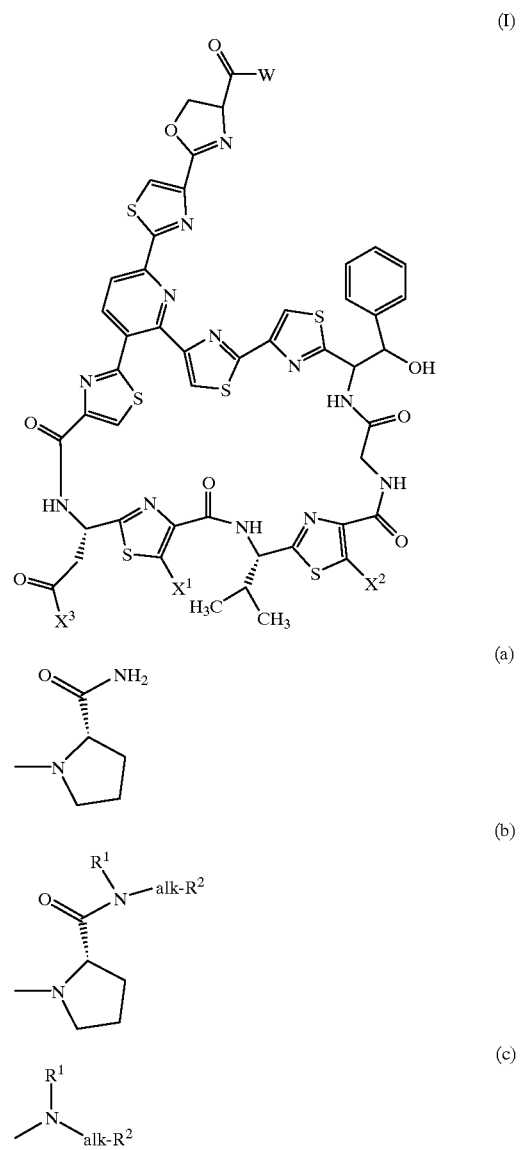

34 Claims, No Drawings

DERIVATIVES OF ANTIBIOTIC GE2270 FACTORS $C_{2A}$, $D_2$ AND E

The present invention refers to derivatives of GE2270 factors $C_{2a}$, $D_2$ and E of general formula I

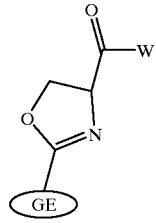

I wherein
W represents a 2-(aminocarbonyl)-pyrrolidinyl moiety of formula

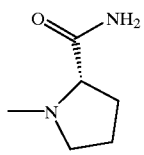

or a group of formula

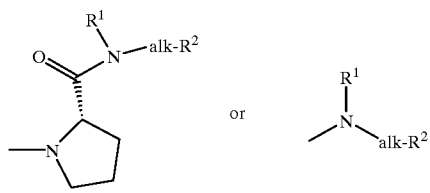

wherein
$R^1$ represents hydrogen or $(C_1-C_4)$alkyl
alk represents $(C_1-C_4)$alkylene
$R^2$ represents
   a $NR^3R^4$ group wherein $R^3$ and $R^4$ independently represent $(C_1-C_4)$alkyl or di$(C_1-C_4)$alkylamino-$(C_1-C_4)$alkylene,
   or a five or six membered heterocycle ring containing one nitrogen atom and optionally a further heteroatom selected from nitrogen and oxygen, optionally substituted with a group selected from $(C_1-C_4)$alkyl, hydroxy$(C_1-C_4)$alkylene, di$(C_1-C_4)$alkylamino or di$(C_1-C_4)$alkylamino-$(C_1-C_4)$alkylene,
   or $R^1$ and alk-$R^2$ together with the adjacent nitrogen atom form a five or six membered heterocycle ring optionally containing a further heteroatom selected from oxygen and nitrogen, optionally substituted with a group selected from $(C_1-C_4)$alkyl, di$(C_1-C_4)$alkylamino, di$(C_1-C_4)$alkylamino$(C_1-C_4)$alkylene, hydroxy$(C_1-C_4)$alkylene, and a alk$_2$-$R^5$ group wherein alk$_2$ is $(C_1-C_4)$alkyl and $R^5$ represents
      a $NR^6R^7$ group wherein $R^6$ and $R^7$ independently represent $(C_1-C_4)$alkyl or di$(C_1-C_4)$alkylamino$(C_1-C_4)$alkylene
      or a five or six membered heterocycle ring containing one or two heteroatoms selected from nitrogen and oxygen, optionally substituted with a group selected from $(C_1-C_4)$alkyl, hydroxy$(C_1-C_4)$alkylene, di$(C_1-C_4)$alkylamino or di$(C_1-C_4)$alkylamino$(C_1-C_4)$alkylene;

the group GE represents the antibiotic core portion of formula

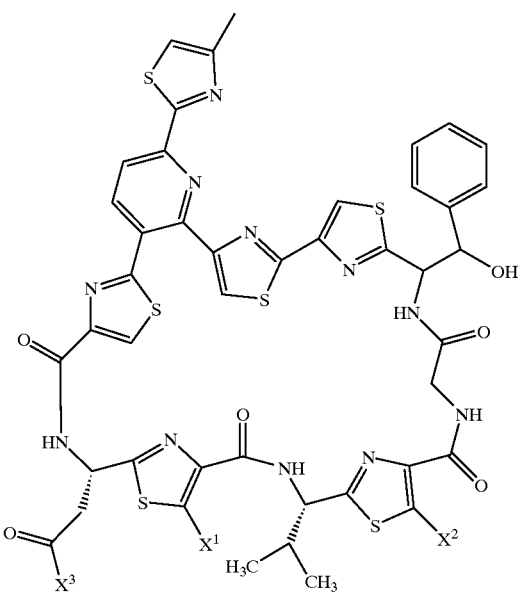

wherein:
$X^1$ is methyl, $X^2$ is a —CH$_2$—$W^1$ moiety and $X^3$ is methylamino or amino, or
$X^1$ is a —CH$_2$—$W^1$ moiety, $X^2$ is methoxymethylene and $X^3$ is methylamino,
wherein $W^1$ represents hydroxy, $(C_1-C_4)$alkylthio or a group $NR^8R^9$ wherein
   $R^8$ represents $(C_1-C_4)$alkyl,
   $R^9$ $(C_1-C_4)$alkyl or di$(C_1-C_4)$alkylamino-$(C_1-C_4)$alkylene
   or $R^8$ and $R^9$ together with the adjacent nitrogen atom form a five or six membered heterocycle ring optionally containing a further heteroatom selected from oxygen and nitrogen, optionally substituted with a group selected from $(C_1-C_4)$alkyl, di$(C_1-C_4)$alkylamino, di$(C_1-C_4)$alkylamino$(C_1-C_4)$alkylene, hydroxy$(C_1-C_4)$alkylene;
with the proviso that when $X^3$ is amino, then W must be 2-(aminocarbonyl)-pyrrolidinyl;
with the further proviso that when W is 2-(aminocarbonyl)pyrrolidinyl, then $W^1$ can not be hydroxy;

and the pharmaceutically acceptable salts thereof.

The present invention refers also to the processes for preparing the compounds of formula I and to the corresponding precursors of the compounds of formula I, wherein the amidic group of said compounds, i.e. the group of formula:

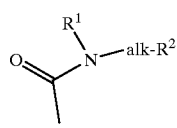

is substituted by the group —COOY, wherein Y represents hydrogen or $(C_1-C_4)$alkyl.

Antibiotic GE2270 is prepared by culturing a sample of *Planobispora rosea* ATCC 53773 or a producing variant or mutant thereof and isolating the desired antibiotic substance from the mycelium and/or the fermentation broth. *Planobispora rosea* ATCC 53773 was isolated from a soil sample and deposited on Jun. 14, 1988 with the American Type Culture Collection (ATCC), 12301 Parklawn Drive, Rockville, Md. 20852 Maryland, U.S.A., under the provisions of the Budapest Treaty. The strain has been accorded accession number ATCC 53773.

Antibiotic GE2270 factor A is the main component of the antibiotic GE2270 complex. Antibiotic GE2270 factor A and *Planobispora rosea* ATCC 53773 are described in U.S. Pat. No. 5139778.

At present, a number of minor factors of antibiotic GE2270 have been isolated, namely factors $B_1$, $B_2$, $C_1$, $C_2$, $D_1$, $D_2$, E and T disclosed in European Patent Application Publication no. 451486 which has as its equivalent, U.S. Pat. No. 5,747,295, which is hereby incorporated by reference and factor $C_{2a}$ disclosed in European Patent Application Publication no. 529410 which has as its equivalent, U.S. Pat. No. 5,514,649, which is hereby incorporated by reference.

Also degradation products of GE2270 factor A are known, namely factors $A_1$, $A_2$, $A_3$ and H disclosed in U.S. Pat. No. 5139778.

Among these compounds, GE2270 factor $C_{2a}$, $D_2$ and E may be employed as suitable starting materials for preparing the compounds of the present invention.

The above factors may be represented by the ollowing formula II

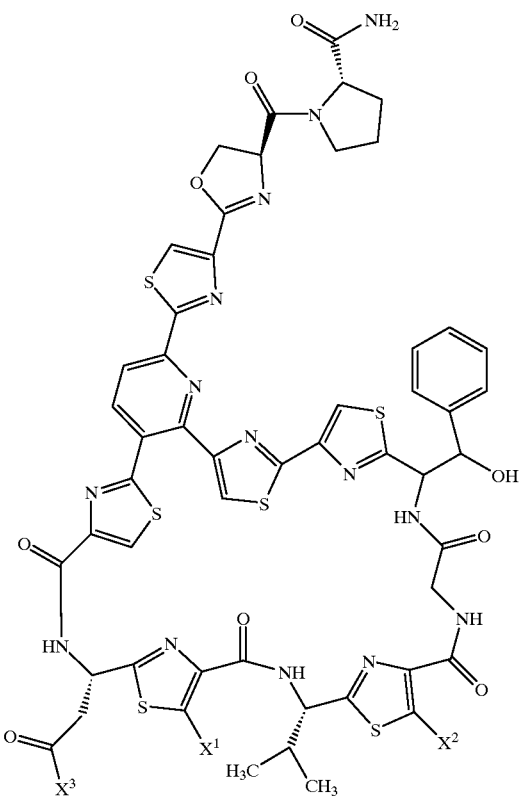

wherein:
$X^1$ is hydroxymethylen, $X^2$ is methoxymethylen and $X^3$ is methylamino for factor $C_{2a}$;
$X^1$ is methyl, $X^2$ is hydroxymethylen and $X^3$ is methylamino for factor $D_2$;
$X^1$ is methyl, $X^2$ is hydroxymethylen and $X^3$ is amino for factor E.

It should be noted that this formula does not correspond to the one disclosed in the above cited Patent Applications. As a matter of fact, further studies on the degradation products of the GE2270 factors (P. Tavecchia et al., Jour. of Antib., 47, no. 12 (1994), 1564–1567) have lead to the conclusion that the surmised aminoacid sequence was not correct, as the two aminoacids bearing the moieties $X^1$ and $X^2$ were actually in an opposite sequence in comparison with the formula previously reported; therefore the present formula II has been proposed for correctly representing the structure of antibiotic GE2270.

GE2270 amide derivatives of general formula

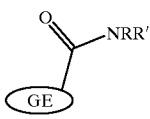

are disclosed in PCT/EP92/00002 (designating also U.S.); also in this case, as above, the disclosed structure of the molecule core is uncorrect. As evident, the above amide derivatives of GE2270 differ from the compounds of the present invention in that the two terminal heterocycle rings of the GE2270 molecule (i.e. the oxazoline and/or the proline rings) are not present in the above general formula.

Furthermore, amide derivatives of GE2270 factors A, $B_2$, $C_1$ and $C_2$, of formula

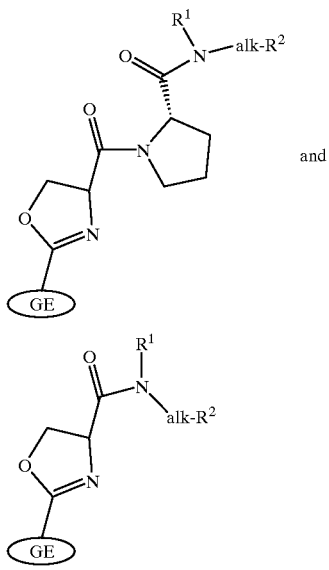

and wherein GE defines the core portion of the GE2270 factors A, $B_2$, $C_2$ and $C_2$, while the groups alk, $R^1$ and $R^2$ are as defined in formula I, are disclosed in the co-pending European Patent International Publication Numbers WO 96/24608 and WO 96/24607.

In the present description, the terms used above in defining the meanings of the substituents are intended to have the meanings commonly assigned to them in the art.

Accordingly;

($C_1$–$C_4$)alkyl represents a linear or branched hydrocarbon moiety containing 1, 2, 3 or 4 carbon atoms such as:
—$CH_3$,
—$CH_2$—$CH_3$,
—$CH_2$—$CH_2$—$CH_3$,
—CH—($CH_3$)$_2$,
—$CH_2$—$CH_2$—$CH_2$—$CH_3$,
—CH($CH_3$)—$CH_2$—$CH_3$,
—$CH_2$—CH($CH_3$)—$CH_3$,
—C—($CH_3$)$_3$;

($C_1$–$C_4$)alkylene represents a bifunctional linear or branched hydrocarbon moiety containing 1, 2, 3 or 4 carbon atoms such as:
—$CH_2$—,
—$CH_2$—$CH_2$—,
—CH($CH_3$)—
—$CH_2$—$CH_2$—$CH_2$—,
—CH($CH_3$)—$CH_2$—,
—$CH_2$—$CH_2$—$CH_2$—$CH_2$—,
—CH($CH_3$)—$CH_2$—$CH_2$—,
—$CH_2$—CH($CH_3$)—$CH_2$—
—C($CH_3$)$_2$—$CH_2$—;

hydroxy($C_1$–$C_4$)alkylene represents a linear or branched alcanolic moiety of from 1 to 4 carbon atom, such as:
—$CH_2$—OH,
—$CH_2$—$CH_2$—OH,
—CH($CH_3$)—OH
—$CH_2$—$CH_2$—$CH_2$—OH,
—CH($CH_3$)—$CH_2$—OH,
—$CH_2$—CH($CH_3$)—OH
—$CH_2$—$CH_2$—$CH_2$—$CH_2$—OH,
—CH($CH_3$)—$CH_2$—$CH_2$—OH,
—$CH_2$—CH($CH_3$)—$CH_2$—OH,
—$CH_2$—$CH_2$—CH($CH_3$)—OH
—C($CH_3$)$_2$—$CH_2$—OH;

di($C_1$–$C_4$)alkylamino, is an amino moiety substituted with two linear or branched alkyl groups containing 1, 2, 3 or 4 carbon atoms such as:
—N—($CH_3$)$_2$,
—N($CH_3$)—($CH_2$—$CH_3$),
—N($CH_2$—$CH_3$)$_2$,
—N($CH_3$)—($CH_2$—$CH_2$—$CH_3$),
—N($CH_2$—$CH_3$)—($CH_2$—$CH_2$—$CH_3$),
—N($CH_2$—$CH_2$—$CH_3$)$_2$,
—N($CH_3$)—[CH—($CH_3$)$_2$],
—N($CH_2$—$CH_3$)—[CH—($CH_3$)$_2$],
—N($CH_3$)—($CH_2$—$CH_2$—$CH_2$—$CH_3$),
—N($CH_2$—$CH_3$)—($CH_2$—$CH_2$—$CH_2$—$CH_3$),
—N($CH_2$—$CH_2$—$CH_3$)—($CH_2$—$CH_2$—$CH_2$—$CH_3$),
—N($CH_2$—$CH_2$—$CH_2$—$CH_3$)$_2$,
—N($CH_2$—$CH_2$—$CH_2$—$CH_3$)—[CH—($CH_3$)$_2$];

a five or six membered heterocycle ring according to the meanings of $R^2$ or $R^5$ is an heterocycle ring such as:

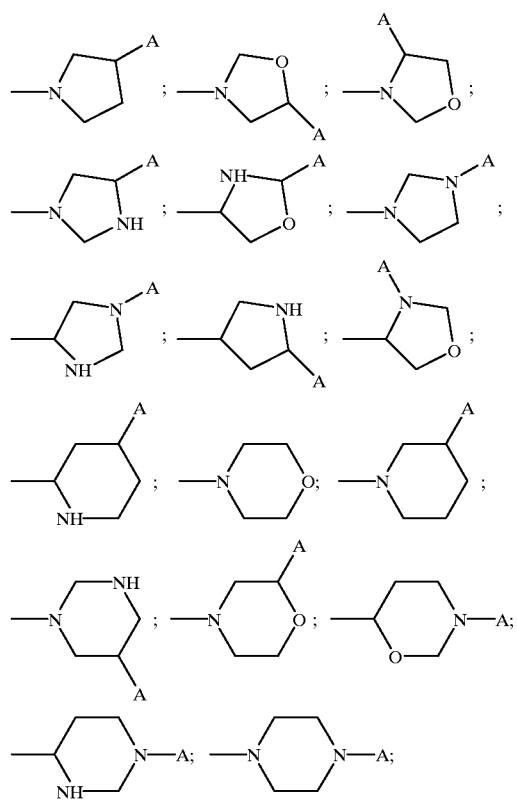

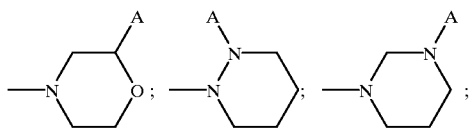

wherein A represents hydrogen or hydroxy($C_1$–$C_4$) alkylene when referring to the substituent "$R^2$" or A represents only hydrogen when referring to the substituent "$R^5$";

a five or six membered heterocycle ring formed by the moieties $R^1$ and alk-$R^2$ together, is an heterocycle ring such as:

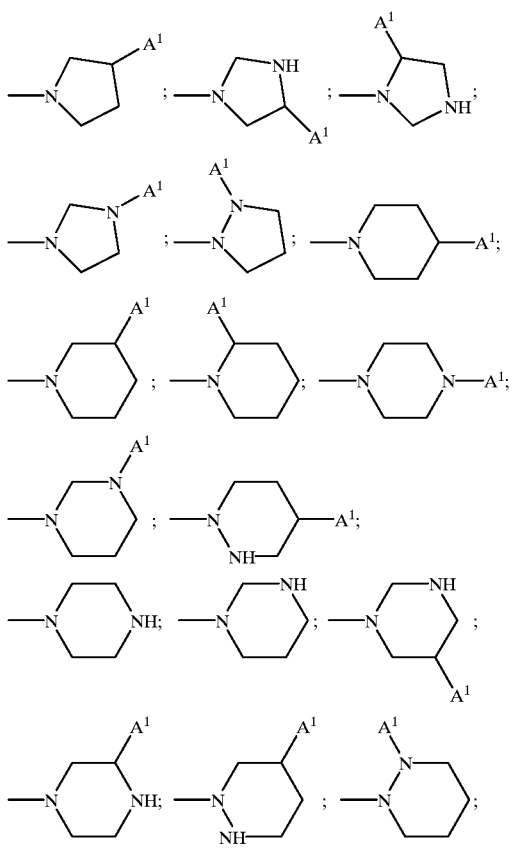

wherein $A^1$ represents hydrogen or the optional substituents of the heterocycle ring as set forth before.

By comparing the above formulas I and II, it appears that GE 2270 factors naturally occur with a determined chirality of the molecule; according to the present invention, the compounds of formula I may be obtained with both the chiralities, with respect to the to the bond between the oxazoline and the proline rings. Although in most cases, the antimicrobial activity of the two epimers (either of the starting materials or of the compounds of the invention) is almost the same, in some cases, against particular strains (e.g. streptococci), it has been observed a slightly higher antimicrobial activity for those compounds having the chirality corresponding to the natural one.

Thus, a group of preferred compounds of the invention are those compounds of general formula Ia

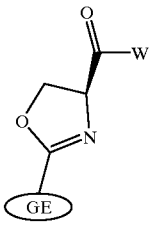

wherein the groups GE and W are as defined in formula I.

Another group of preferred compounds are those compounds of formula I or Ia, the moiety W being as defined in formula I wherein $R^1$ represents hydrogen or ($C_1$–$C_4$)alkyl, alk represents ($C_1$–$C_4$)alkylene $R^2$ represents a $NR^3R^4$ group wherein $R^3$ and $R^4$ independently represent ($C_1$–$C_4$)alkyl or di($C_1$–$C_4$) alkylamino-($C_1$–$C_4$)alkylene.

A further group of preferred compounds are those compounds of formula I wherein the moiety GE is as defined in formula I or Ia, $X^1$, $X^2$ and $X^3$ being as defined, $W^1$ representing hydroxy, ($C_1$–$C_4$)alkylthio or a group $NR^8R^9$ wherein $R^8$ is ($C_1$–$C_4$)alkyl, and $R^9$ is ($C_1$–$C_4$)alkyl or di($C_1$–$C_4$)alkylamino-($C_1$–$C_4$)alkylene.

Examples of moieties according to the —($R^1$)alk$R^2$ group, as defined under the meanings of the W substituent in formula I, are the following:

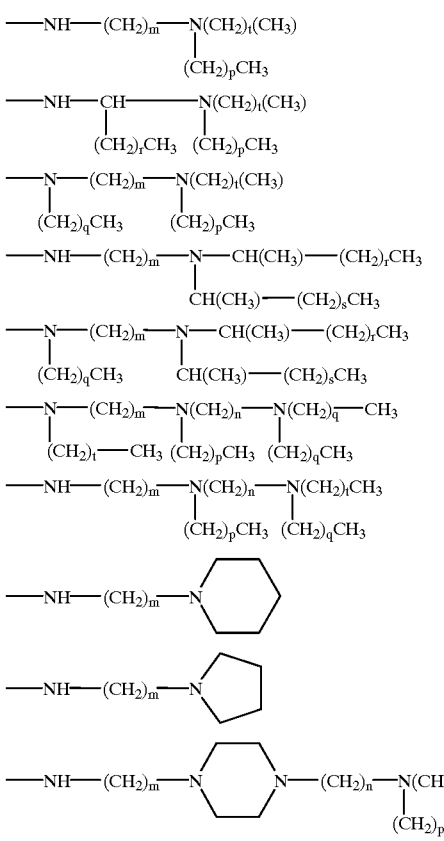

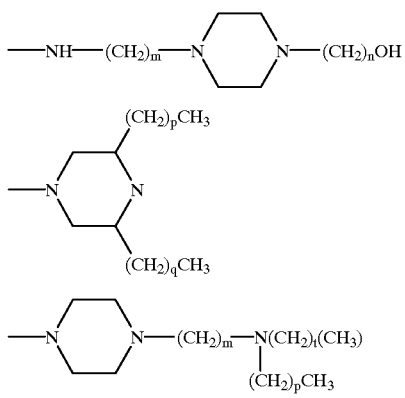

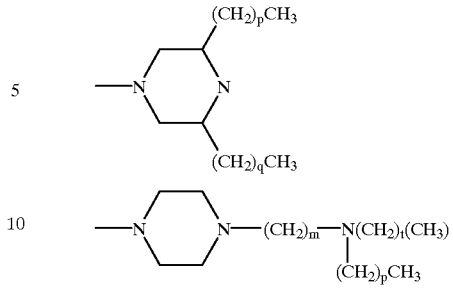

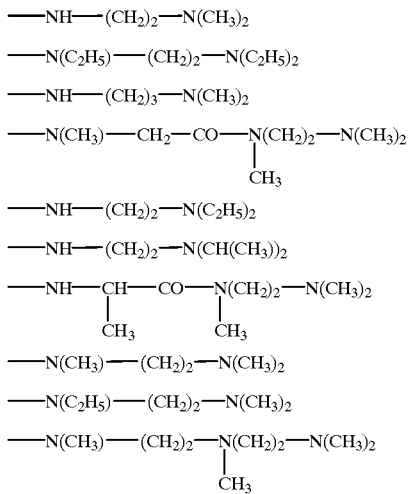

wherein:

m and n=1, 2, 3 or 4;

p, q and t=0, 1, 2 or 3 r and s=0 or 1.

Preferred examples of —N(R$^1$)alkR$^2$ groups are the following:

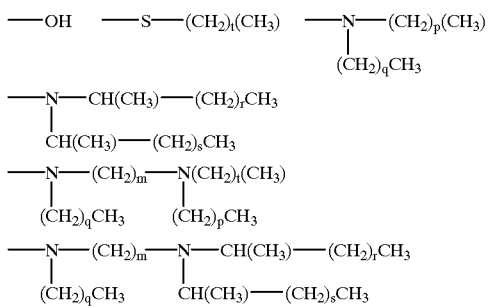

Examples of moieties according to the subbstituent W$^1$, as defined under the meanings of the GE moiety in formula I, are the following:

—OH  —S—(CH$_2$)$_t$(CH$_3$)  —N—(CH$_2$)$_p$(CH$_3$)
                                                   |
                                                 (CH$_2$)$_q$CH$_3$

—N—CH(CH$_3$)—(CH$_2$)$_r$CH$_3$
|
CH(CH$_3$)—(CH$_2$)$_s$CH$_3$

—N—(CH$_2$)$_m$—N(CH$_2$)$_t$(CH$_3$)
|                   |
(CH$_2$)$_q$CH$_3$   (CH$_2$)$_p$CH$_3$

—N—(CH$_2$)$_m$—N—CH(CH$_3$)—(CH$_2$)$_r$CH$_3$
|                |
(CH$_2$)$_q$CH$_3$  CH(CH$_3$)—(CH$_2$)$_s$CH$_3$ wherein:

m and n=1, 2, 3 or 4;

p, q and t=0, 1, 2 or 3 r and s=0 or 1.

Preferred examples of W$^1$ groups are the following:

—OH  —S—(CH$_2$)(CH$_3$)

—N(C$_2$H$_5$)$_2$  —N(CH$_3$)$_2$  —N(CH$_3$)—(CH$_2$)$_2$—N(CH$_3$)$_2$

The compounds of the invention can form salts according to conventional procedures.

In particular, those compounds of formula I wherein the group —N(R$^1$)alkR$^2$ contains further amine functions can form acid addition salts.

Preferred addition salts are the pharmaceutically acceptable acid addition salts.

With the term "pharmaceutically acceptable acid addition salts" are intended those salts with acids which from biological, manufacturing and formulation standpoint are compatible with the pharmaceutical practice as well as with the use in the animal growth promotion.

Representative and suitable acid addition salts of the compounds of formula I include those salts formed by standard reaction with organic or inorganic acids such as, hydrochloric, hydrobromic, sulfuric, phosphoric, acetic, trifluoroacetic, trichloroacetic, succinic, citric, ascorbic, lactic, maleic, fumaric, palmitic, cholic, pamoic, mucic, glutamic, camphoric, glutaric, glycolic, phthalic, tartaric, lauric, stearic, salicylic, methanesulfonic, dodecylsulfonic (estolic), benzenesulfonic, sorbic, picric, benzoic, cinnamic acid and the like.

The transformation of the free amino or non-salt compounds of the invention into the corresponding addition salts, and the reverse, i.e. the transformation of an addition salt of a compound of the invention into the non-salt or free amino form, are within the ordinary technical skill and are encompassed by the present invention. The only precaution is to avoid solutions with pH lower than 4–5 when preparing the addition salt (for avoiding the opening of the oxazolinic ring) and solutions with a pH higher than 8–9 when freing the base (for avoiding epimerization at the oxazoline chiral center).

For instance, a compound of formula I can be transformed into the corresponding acid or base addition-salt by dissolving the non-salt form in an aqueous solvent and adding a slight molar excess of the selected acid. The resulting solution or suspension is then lyophilized to recover the desired salt. Instead of lyophilizing, in some instances, it is possible to recover the final salt by extraction with an organic solvent, concentration to a small volume of the separated organic phase and precipitation by adding a non-solvent.

In case the final salt is unsoluble in an organic solvent where the non-salt form is soluble, it may be recovered by filtration from the organic solution of the non-salt form after addition of the stoichiometric amount or a slight molar excess of the selected acid.

The non-salt form can be prepared from a corresponding acid salt dissolved in an aqueous solvent which is then neutralized to free the non-salt form. This is then recovered for instance by extraction with an organic solvent or is transformed into another acid addition salt by adding the selected acid and working up as above.

A common desalting procedure may be employed when, following the neutralization, desalting is necessary.

For example, column chromatography on controlled pore polydextrane resins (such as Sephadex LH 20) or silanized silica gel may be conveniently used. After eluting the undesired salts with an aqueous solution, the desired product is eluted by means of linear gradient or step-gradient of a mixture of water and a polar or apolar organic solvent, such as acetonitrile/water from 50:50 to about 100% acetonitrile.

As is known in the art, the salt formation either with pharmaceutically acceptable acids or non-pharmaceutically acceptable acids may be used as a convenient purification technique. After formation and isolation, salt form of a compound of formula I can be transformed into the corresponding non-salt or into a pharmaceutically acceptable salt.

In some instances the acid addition salt of a compound of formula I is more soluble in water and hydrophilic solvents and has an increased chemical stability. Good solubility and stability in water or hydrophylic solvents of an active compound are in general appreciated in the art, for the preparation of suitable pharmaceutical compositions for the administration of the medicament.

However, in view of the similarity of the properties of the compounds of formula I and their salts, what is said in the present application when dealing with the biological activities of the compounds of formula I applies also to their pharmaceutically acceptable salts, and viceversa.

According to formula I, the present invention provides either mono- or di-substituted derivatives of antibiotic GE2270. In particular, it is possible to prepare:

a) di-substituted derivatives of factors $C_{2a}$ or $D_2$, according to the substituent defined for W (other than aminocarbonyl-pyrrolidinyl) and $W^1$ (other than hydroxy) in formula I;

b) mono-substituted derivatives of factors $C_{2a}$ or $D_2$, according to the substitutents defined for W (other than aminocarbonyl-pyrrolidinyl) in formula I, while $W^1$ is hydroxy;

c) mono-substituted derivatives of the factors $C_{2a}$, $D_2$ or E, according to the meanings of $W^1$ (other than hydroxy) in formula I, while W is the unsubstituted aminocarbonyl-pyrrolidinyl moiety of GE2270.

The insertion of the W (or $W^1$) moieties may be carried out either on the unsubstituted molecule of the suitable GE2270 factor, thus obtaining a mono-substituted derivative, or on the corresponding $W^1$- or W-substituted factor, thus obtaining a di-substituted derivative.

Accordingly, the following preparation methods A, B and C thus refer to the insertion of the W moiety on the molecule of unsubstituted or $W^1$-substituted GE2270 factors $C_{2a}$ or $D_2$, while method D refers to insertion of the $W^1$ moiety on the molecule of GE2270 factor E or on the molecule of unsubstituted or W-substituted GE2270 factors $C_{2a}$, $D_2$.

A suitable method for preparing the compounds of the invention ("Method A") thus comprises:

a) reacting a compound of formula III

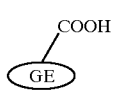

III wherein the group GE is as defined in formula I, $X^1$ and $X^2$ being as defined and $X^3$ being methylamino, with the proviso that when $W^1$ is hydroxy it must be protected with a suitable protecting group removable under neutral deprotecting conditions, with a suitable serinamide of formula IVa or IVb:

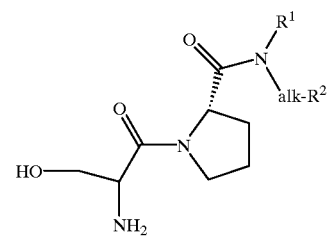

IVa

IVb wherein $R^1$, alk and $R^2$ are as in formula I, in an inert aprotic organic solvent in the presence of a condensing agent;

b) cyclizing the serine moiety of the obtained compound of formula IIIa or IIIb:

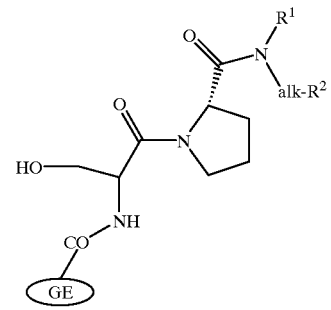

IIIa

IIIb with a suitable cyclizing reactant, in order to obtain the desired oxazoline ring;

c) removing, if present, the protective group of the —OH moiety.

According to method A, the chirality of the final compound is determined by the chirality of the serinamide reactant employed, with retention of the configuration of the serine chiral center. Thus, for obtaining the amide derivatives with a chirality corresponding to the natural one, L-serinamides shall be employed.

With this method it is thus possible to prepare di-substituted derivatives of GE2270 factor $C_{2a}$ or $D_2$ wherein W and $W^1$ are as defined in formula I, by starting from the corresponding $W^1$-substituted compounds, or mono-substituted derivatives of these two factors, wherein W is as defined in formula I and $W^1$ is hydroxy.

Inert organic aprotic solvents useful for the condensation reaction according to method A are those solvents which do not unfavorably interfere with the reaction course and are capable of at least partially solubilizing the antibiotic starting material.

Examples of said solvents are organic amides, ethers of glycols and polyols, phosphoramides, sulfoxides and mitures thereof. Preferred examples are: dimethylformamide, dimethoxyethane, hexamethylphosphoramide, dimethylsulfoxide, dioxane, and mixtures thereof. Preferably, dimethylformamide (DMF) is employed.

The condensing agent in the present method is one suitable for forming amide bonds in organic compounds and in particular in peptide synthesis.

Representative and preferred examples of condensing agents are $(C_1-C_4)$alkyl, phenyl or heterocyclic phosphorazidates such as, diphenyl-phosphorazidate (DPPA), diethyl-phosphorazidate, di(4-nitrophenyl)-phosphorazidate, dimorpholyl-phosphorazidate and diphenylphosphorochloridate or benzotriazol-1-yl-oxy-tripyrrolidinophosphoniumhexa-fluorophosphate (PyBOP). The preferred condensing agent is DPPA.

The condensing agent is generally employed in a slight molar excess with respect to the starting antibiotic material, such as from 1.1 to 1.5 times; preferably the molar excess of condensing agent is 1.2 times the amount of antibiotic GE2270 starting compound.

According to the present method, the serinamide of formula IVa or IVb is also in general used in a slightly molar excess, with respect to the starting antibiotic compound.

In general, a 1 to 1.5 fold molar excess is used, while a 1.2 fold molar excess is preferred.

For the amidation to proceed, it is necessary that the serinamide of formula IVa or IVb is capable of forming a salt with the carboxy function of the antibiotic starting material. As this could require the use of a higher amount of serinamide, in such a case it is convenient to add a salt-forming base to the reaction mixture, at least in an equimolecular amount, and preferably a 2 to 3 fold molar excess, with respect to the antibiotic starting material.

Examples of said salt-forming bases are tertiary organic aliphatic or alicyclic amines such as trimethylamine, triethylamine (TEA), N-methyl pyrrolidine or heterocyclic bases such as picoline, and the like.

In addition, the serinamide of formula IVa or IVb may also conveniently be introduced in the reaction medium as a corresponding acid addition salt, such as hydrochloride, trifluoroacetate, and the like. In fact, at least in some instances, the use of the salified serinamide, which is then freed in situ with the above mentioned bases, is preferred, particularly when the salt is more stable than the corresponding free amine. In this case, at least a double molar proportion and preferably a 2 to 3 fold molar excess of a strong base capable of freeing the serinamide of formula IVa or IVb from its salts, is used. Also in this case, the suitable base is a tertiary organic aliphatic or alicyclic amine like those exemplified above, preferably TEA.

The reaction temperature will vary considerably depending on the specific starting materials and reaction conditions. In general, it is preferred to conduct the reaction at temperatures from 0° C. to room temperature, preferably starting at about 0° C. and allowing the mixture to reach room temperature during the reaction.

Also the reaction time varies considerably depending on the other reaction parameters; in general the condensation is completed in about 5–24 h.

Generally, the reaction course is monitored by TLC or preferably by HPLC according to methods known in the art. On the basis of the results of these assays a man skilled in the art will be able to evaluate the reaction course and decide when to stop the reaction and start working up the reaction mass according to known per se techniques. For instance the reaction mixture may be poured into an aqueous basic solution for precipitating the compound of formula IIIa or IIIb as an addition salt. The basic solution should have a pH suitable for precipitating the salt of the desired compound, without modifying its chemical structure. In general, the pH ranges from 8 to 10, and is obtained with an aqueous solution of an inorganic base, such as alkali or alkaline-earth metal hydroxides, carbonates, bicarbonates, and the like. The compound of formula IIIa or IIIb is obtained as a crude, after filtration and evaporation of the above basic solution, as the purification step is preferably accomplished after the cyclization reaction. However, when a purified product is desired, the known per se separation and purification techniques may be employed, which include, for instance, extraction with solvents, precipitation by pH modification, precipitation by addition of non-solvents, etc., in conjunction with further separations and purifications by column chromatography.

Step b) of the present process, i.e. the serine-oxazoline cyclization is performed according to methods known per se in the art.

According to a preferred embodiment, the compound of formula IIIa or IIIb is reacted with methoxycarbonyl-sulfamoyl-triethylammonium hydroxide, inner salt (Burgess reagent), and the reaction mixture is then refluxed for obtaining the oxazoline cyclization.

More in detail, the obtained compound of formula IIIa or IIIb is reacted with an excess (about 3:1 to 15:1) of Burgess reagent, in the presence of an organic aprotic oxygenated solvent, for obtaining the corresponding sulfamoyl ester of the Burgess reactant.

Examples of organic aprotic oxygenated solvents are saturated linear or cyclic ethers or glycol ethers. Preferred examples of said solvents are tetrahydrofuran (THF), dioxane. Optionally chlorinated solvents may also be added to the reaction mixture, such as dichloromethane ($CH_2Cl_2$), chloroform, for increasing the solubility of the reactants.

Optionally, a base may also be added to the reaction mixture, for avoiding undesired side-reactions. Examples of suitable bases are tertiary organic aliphatic or alicyclic amines such as trimethylamine, triethylamine (TEA), N-methyl pyrrolidine or heterocyclic bases such as picoline, and the like; preferably TEA is employed.

The reaction temperature will vary considerably depending on the specific starting materials and reaction conditions. In general, it is preferred to conduct the reaction at temperatures of from 18° C. to 30° C., preferably at room temperature.

Also the reaction time varies considerably depending on the other reaction parameters; in general the reaction is completed in about 4 to 20 hours.

Generally, the reaction course is monitored by TLC or preferably by HPLC according to methods known in the art.

After the reaction is completed, a secondary or tertiary alcohol is added to the reaction mixture, for quenching the reaction. Said alcohol should be able to react with the unreacted Burgess reactant and be transformed in olefinic compounds, preferably low boiling olefines. Thus, a secondary or tertiary ($C_3$–$C_5$)alcohol may suitably be employed, such as isopropanol, tert-butanol, 1-methyl-propanol, 1,1-dimethyl-propanol, 1,2-dimethyl-propanol, 1-ethyl-propanol; preferably, isopropanol is employed.

The reaction mixture is then refluxed for cyclizing the oxazoline. Time and temperature of the reflux will vary mainly depending on the solvents present in the reaction mixture. For instance, if low boiling solvents (e.g. alcohols, chlorinated solvents) are removed before refluxing, higher reflux temperatures are obtained. Thus, depending on the type of solvents present in the refluxing mixture, the temperature will vary from 50° C. to 80° C. In general, as the higher the reflux temperature, the shorter the time, the reflux time will accordingly vary from 20 to 5 hours.

Also in this case, the reaction course is monitored by TLC or preferably by HPLC according to methods known in the art. On the basis of the results of these assays a man skilled in the art will be able to decide when to stop the reflux and start working up the reaction mass according to known per se techniques, which include, as above, extraction with solvents, precipitation by pH modification, precipitation by addition of non-solvents, etc., in conjunction with further chromatographic separations and purifications techniques, such as flash chromatography (e.g. on silica gel using dichloromethane/methanol mixtures as eluent), reverse phase chromatography or chromatography on neutral aluminium oxide (using dichloromethane/methanol mixtures as eluent).

The deprotection step c), when necessary, is performed according to known per se techniques depending on the specific protecting group employed (see T. W. Greene and P. G. M. Wuts, "Protective Groups in Organic Synthesis", 1991 $2^{nd}$ Ed., John Wiley & Sons Inc.), anyway always under neutral deprotecting conditions which would not negatively affect the formed product (e.g. hydrolization or transformation of the oxazoline ring or racemization of its chiral center). For instance, when nitrobenzyl ether or allyl carbonate is employed as protecting group, they may be removed by UV irradiation (at 280–320 nm) or with tetrakis (triphenylphosphine)Pd(O), respectively.

The starting material of formula III may be obtained by hydrolyzing a compound of formula V

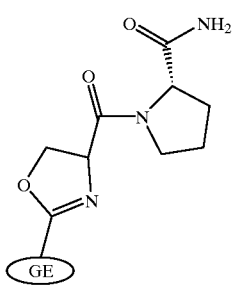

V wherein GE is as defined above, according to the procedure disclosed in International Patent Application Publ. No. PCT/EP92/00002 (designating also U.S.).

If necessary (i.e. when the group $W^1$ of GE is hydroxy), before carrying out the process according to method A, the $W^1$ moiety of the hydrolyzed compound is first protected with a protecting group removable under neutral deprotecting conditions.

Examples of these protecting groups are p-methoxyphenyl, p-methoxybenzyl and o-nitrobenzyl ethers, 2,2,2-trichloroethyl, 2-(trimethylsilyl)ethyl and allyl carbonates; preferred are o-nitrobenzyl ethers and allyl carbonates.

The protection of the hydroxy moiety is accomplished according to procedures known in the art, depending on the specific protecting group employed (see the above cited "Protective Groups in Organic Synthesis"). For instance, when allyl carbonate is employed as a protecting group, then diallylpirocarbonate is reacted with the GE2270 starting material in THF in the presence of pyridine and a catalytic amount of N,N-dimethylamino-pyridine (DMAP) at room temperature.

The serinamide of formula IVa or IVb is prepared according to known per se techniques of peptide synthesys, described in a number of references books like E. Gross and J. Meienhofer "The Peptides", Vol. 3, Academic Press, New York, 1981 and M. Bodanszky and A. Bodanszky "The Practice of Peptide Synthesis, Springer-Verlag, Berlin Heidelberg, 1984.

As a general procedure, for preparing a serinamide of formula IVa, a N-protected proline is first reacted with the desired amine of formula VI

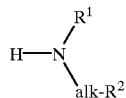

VI wherein $R^1$, alk, and $R^2$ are as defined in formula I; the obtained prolinamide is then deprotected and reacted with a N-protected serine, to give the desired N-protected starting material. As said above, when amide derivatives of formula I with a chirality corresponding to the natural one are desired, L-serinamides shall be employed; accordingly, the prolinamide shall be reacted with N-protected L-serine.

As known in the the art, the amidation reactions may either be performed in the presence of a condensing agent (e.g. phosphorazidates such as diphenilphosphorazidate, DPPA) or the N-protected amino acid may be reacted in the form of an activated ester (such as pentafluorophenyl, N-hydroxysuccynimide or 1-hydroxybenzothiazole ester).

The protecting group employed in both steps of the above described process are those generally employed in peptides synthesis. Preferably, the N-protection of serine is performed with protecting group which are easily removable under acid or neutral hydrolitic conditions, such as t-butoxycarbonyl (BOC) or benzyloxycarbonyl (cbz).

In a similar way, a serinamide of formula IVb is prepared by reacting the above amine of formula VI with N-protected serine (or L-serine), under the above described conditions.

Preferably, the N-deprotection of the serinamide is performed only short before the amidation reaction with the GE2270 starting material, so to avoid the formation of undesired side products.

The amines of general formula VI are either commercially available compounds or may be prepared according to known per se techniques, described in a number of references books, such as "Comprehensive Organic Syhthesis, vol. 8, 1991, Pergamon Press".

Another suitable method (hereinafter defined as "Method B") for preparing the compounds of the invention is to react a compound of formula VII

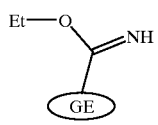

VII wherein the group GE is as defined in formula I, $X^1$ and $X^2$ being as defined and $X^3$ being methylamino, with a serinamide of formula IVa or IVb as above defined under method A, in a protic organic solvent.

Also in this case as in method A, the chirality of the final compound is determined by the chirality of the serinamide reactant employed, with retention of the configuration of the serine chiral center.

As above, with method B it is possible to prepare di-substituted derivatives of GE2270 factor $C_{2a}$ or $D_2$ of formula I wherein W and $W^1$ are as defined in formula I, by starting from the corresponding $W^1$-substituted factors, or mono-substituted derivatives of these two factors, wherein W is as defined in formula I and $W^1$ is hydroxy.

Preferred protic organic solvents are those solvents which do not unfavourably interfere with the reaction course and are capable of at least partially solubilizing the antibiotic starting material. Preferred examples of such solvents are $(C_1–C_4)$alcohols, such as methanol, ethanol, propanol, iso-propanol, butanol, iso-butanol and mixtures thereof.

Preferably, also minor amounts of an aprotic organic solvent are added, for increasing the solubility of the GE 2270 starting material; preferred solvents are in this case chlorinated solvents, particularly preferred being dichloromethane.

Furthermore, as the serinamide of formula IVa or IVb is preferably employed in the form of acid addition salt, a base as defined before is preferably added to the reaction mixture. The total amount of base will depend on the number of salified aminic groups of serinamide; as a general rule, if "n" is the number of equivalents of salified aminic groups, then about "n−1" equivalents of base are added.

Examples of said bases are, as above, tertiary organic aliphatic or alicyclic amines such as trimethylamine, triethylamine (TEA), N-methyl pyrrolidine or heterocyclic bases such as picoline, and the like, preferred being TEA.

The reaction temperature will vary considerably depending on the specific starting materials and reaction conditions. In general, it is preferred to conduct the reaction at temperatures of from 15° C. to 30° C., conveniently at room temperature.

Also the reaction time varies considerably depending on the other reaction parameters; in general the condensation is completed in about 20–40 h.

Generally, the reaction course is monitored by TLC or preferably by HPLC according to methods known in the art. On the basis of the results of these assays a man skilled in the art will be able to evaluate the reaction course and decide when to stop the reaction and start working up the reaction mass according to known per se techniques, which include, as above, extraction with solvents, precipitation by pH modification, precipitation by addition of non-solvents, etc., in conjunction with further chromatographic separations and purifications techniques, such as flash chromatography (e.g. on silica gel using dichloromethane/methanol mixtures as eluent), reverse phase chromatography or chromatography on neutral aluminium oxide (using dichloromethane/methanol mixtures as eluent).

A suitable method for preparing the starting material of formula VII is described in the cited International Patent Application Publ. No. PCT/EP92/00002; in said document it is specifically disclosed the preparation of the correspondent derivative of formula VII of GE2270 factor A; however, the same procedure can be applied to GE2270 factors $C_{2a}$ or $D_2$ (corresponding to the above formula V wherein $W^1$ is hydroxy) or to the derivatives thereof obtainable according to method D described hereinafter.

According to said preparation, factors $C_{2a}$ or $D_2$, or to the derivatives thereof obtainable according to method D described hereinafter, are first hydrolyzed under suitable conditions (e.g. with acetic acid in ethanol, at 60° C. for 24 hours), for obtaining the corresponding hydrolyzed derivatives of formula VIII

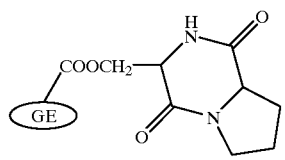

VIII wherein GE is as defined in formula I; this compound is then reacted with ammonia in the presence of an organic protic solvent, preferably $(C_1–C_4)$alcohol, particularly preferred being methanol. After about 2 to 4 days, preferably 3 days, the solution is evaporated and the residue is worked up according to the above known per se techniques, thus obtaining the respective amide derivative of formula:

The obtained compound is in turn reacted with a solution of Burgess reagent in an organic aprotic solvent. The only precaution that should be taken is that when the group $W^1$ of GE is hydroxy or mercapto it should be protected with a suitable protecting group removable under basic or mild acid conditions, such as $(C_1–C_4)$alkyl or aromatic esters (e.g. acetyl, propionyl, pivaloyl and nitrobenzyl), t-butoxycarbonyl, carbobenzyloxy, and the like; other suitable protecting groups can be found in the cited reference book "Protecting groups in organic synthesis". Preferably, the acyl protecting group is employed.

Suitable solvents are cyclic or glycol ethers such as THF or dioxane or chlorinated solvents such as dichloromethane $(CH_2Cl_2)$ or chloroform, or mixtures thereof; preferably $CH_2Cl_2$ is employed.

Furthermore, a base is optionally added to the reaction mixture, as previously described; preferably triethylamine is employed.

Optionally, further Burgess reagent may be added to the reaction mixture after 12 to 20 hours, preferably after 16 hours.

The reaction temperature, depending on the other reaction parameters, may vary from 18° C. to 30° C., preferably at room temperature.

Also the reaction time varies considerably depending on the other reaction parameters; in general the reaction is completed in about 12 to 36 hours after the last addition of Burgess reagent.

Generally, the reaction course is monitored by TLC or preferably by HPLC according to methods known in the art. On the basis of the results of these assays a man skilled in the art will be able to decide when to stop the reaction and start working up the reaction mass according to known per se techniques, which include, as above, extraction with solvents, precipitation by pH modification, precipitation by addition of non-solvents, etc., in conjunction with further chromatographic separations and purifications techniques, such as flash chromatography (e.g. on silica gel using dichloromethane/methanol mixtures as eluent).

When the obtained compound contains a protecting group of the hydroxy function, this group is removed according to methods known in the art. For instance, when the protecting group is acetyl, it is removed by basic hydrolysis with aqueous sodium hydroxide in cyclic or glycol ethers such as dioxane or tetrahydrofurane.

The corresponding nitrile derivative of formula is thus obtained, which is then dissolved in ethanol, preferably in the presence of a chlorinated

co-solvent (e.g. dichloromethane, chloroform), and the solution is cooled at about 0° C.; dry HCl is then bubbled through the solution for from 4 to 8 hours, preferably for 6 hours.

The reaction mixture is preferably allowed to stay at about 4° C. for from 10 to 18 hours, and then poured into a buffering basic solution for neutralizing the excess of HCl; such solution, having a pH lower than 10, is generally a phosphate or carbonate buffer, preferably a carbonate buffer, particularly preferred being a saturated aqueous solution of sodium carbonate.

The solid which precipitates is worked up according to the above known per se techniques, thus obtaining the desired starting material of formula VII.

A further method for preparing the compounds of the invention (hereinafter defined as "Method C") is to react a compound of formula IXa or IXb

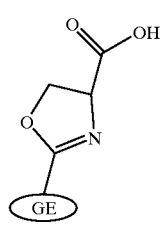

IXa

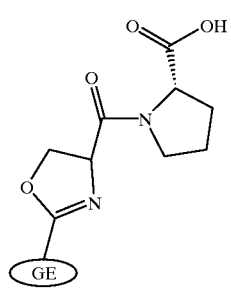

IXb wherein the group GE is as defined in formula I, $X^1$ and $X^2$ being as defined and $X^3$ being methylamino, with an amine of formula VI:

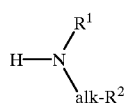

VI wherein $R^1$, alk, and $R^2$ are as defined in formula I, in the presence of an inert organic solvent and of a condensing agent.

Also with method C it is possible to prepare di-substituted derivatives of GE2270 factor $C_{2a}$ or $D_2$ of formula I wherein W and $W^1$ are as defined in formula I, by starting from the corresponding $W^1$-substituted factors, or mono-substituted derivatives of these two factors wherein W is as defined in formula I and $W^1$ is hydroxy.

According to this method, the final compound is in general obtained as an epimeric mixture, with respect to the configuration of the serine chiral center.

Useful inert organic aprotic solvents are as defined for method A.

Also type and amounts of condensing agent are those defined for the condensation reaction of method A.

The starting material of formula IXa or IXb is preferably used in its salified form, preferably as an alkali metal salt, particularly preferred being the sodium salt. Thus, a strong acid is conveniently added to the reaction mixture, for freeing the compound from its salt; in general a 2 fold excess of acid equivalents are preferably added. Examples of strong acids are hydrohalide acids or sulfuric acid; preferred beeing hydrochloric acid.

As above, a salt-forming base is preferably added to the reaction mixture; type and amount of such base will vary depending on the parameters defined above (i.e. amount of reacting amine and use of salified amine), as well as on the presence of the above defined strong acid; if said acid is present, at least an equivalent amount of base for each equivalent of acid is further on added to the reaction mixture.

The reaction temperature will vary considerably depending on the specific starting materials and reaction conditions. In general, it is preferred to conduct the reaction at temperatures between 15° and 30° C., conveniently at room temperature.

Also the reaction time varies considerably depending on the other reaction parameters. In general the condensation reaction is completed in about 10–16 h.

Generally, the reaction course is monitored by TLC or preferably by HPLC according to methods known in the art. On the basis of the results of these assays a man skilled in the art will be able to evaluate the reaction course and decide when to stop the reaction and start working up the reaction mass according to known per se techniques, which include, as above, extraction with solvents, precipitation by pH modification, precipitation by addition of non-solvents, etc., in conjunction with further chromatographic separations and purifications techniques, such as flash chromatography (e.g. on silica gel using dichloromethane/methanol mixtures as eluent), reverse phase chromatography or chromatography on neutral aluminium oxide (using dichloromethane/methanol mixtures as eluent).

A suitable method for preparing the starting material of formula IXa is to react a solution of the starting material of general formula VII (see method B) in ethanol, preferably in the presence of a chlorinated co-solvent (e.g. dichloromethane, chloroform), with a serine ($C_1$–$C_4$)alkyl ester salt, preferably methyl ester hydrochloride. The reaction temperature varies from 15° C. to 30° C., preferably about room temperature; the reaction time is from 3 to 5 days, preferably about 4 days.

The reaction mixture is then worked up according to known per se techniques, and the solid obtained is purified by means of known chromatographic techniques, preferably by chromatography on silica gel, thus obtaining the compound of formula: wherein Y represents $(C_1-C_4)$alkyl.

The above compound is then dissolved in an inert organic solvent (e.g. alkylamides, alkylnitriles, saturated linear or cyclic ethers, glycol ethers, phosphoramides, chlorinated solvents or mixtures thereof; preferably dioxane) and hydrolyzed with a strong base, such as an alkali or alkaline-earth metal

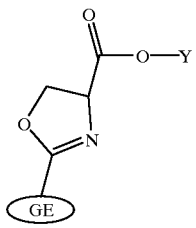

hydroxide, preferably sodium hydroxide, obtaining the sodium salt of the desired carboxylic acid of formula IXa, which may be recovered according to known per se techniques, for instance by addition of non-solvents, preferably ethyl ether. The hydrolysis provokes the epimerization of the chiral center of the oxazoline ring of compound IXa.

For preparing the starting material of formula IXb, the obtained compound IXa (epimeric mixture) is further reacted with L-proline $(C_1-C_4)$alkyl ester, preferably methyl ester, in an inert aprotic organic solvent in the presence of a condensing agent; organic solvent and condensing agent are as previously defined in the condensation reaction of method A.

Optionally, a salt-forming base and a strong acid, as in method A and B, are also added to the reaction mixture. The reaction temperature will vary from 15° C. to 30° C., preferably being about room temperature, for a time reaction of from 10 to 16 hours. The reaction mixture is then worked up according to known per se techniques and the solid obtained is purified by means of known chromatographic techniques, preferably by means of flash chromatography, thus obtaining the compound of formula

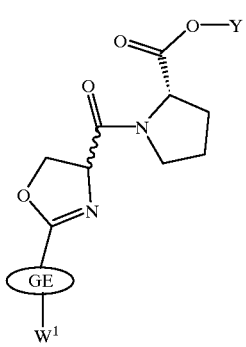

wherein Y represents $(C_1-C_4)$alkyl.

The obtained compound is finally dissolved in an organic solvent (e.g. alkylamides, alkylnitriles, saturated linear or cyclic ethers, glycol ethers, phosphoramides, chlorinated solvents or mixtures thereof; preferably dioxane) and hydrolyzed with a strong base, such as an alkali or alkaline-earth metal hydroxide, preferably sodium hydroxide, obtaining the sodium salt of the desired carboxylic acid of formula IXb, which may be recovered according to known per se techniques, for instance by addition of non-solvents, preferably ethyl ether.

The starting materials IXa and IXb obtained according to the above procedure are in general a mixture of two epimers. This mixture may be separated or employed as such for the condensation reaction with the amine, thus obtaining an epimeric mixture of the compounds of the invention.

If desired, the epimeric mixture may be separated (either before or after the condensation reaction) according to known Per se techniques, such as by reverse phase HPLC, chromatography on neutral or basic aluminium oxide or HPLC on chiral phases.

A suitable method for preparing the $W^1$-susbtituted compounds of the invention (method D) comprises reacting a compound of formula X

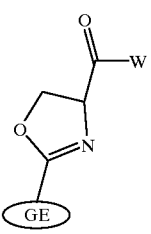

X wherein
W and GE are as defined in formula I, $W^1$ being a suitable leaving group (—OG), with the proviso that when GE represents the core portion of factor E, then W must be 2-(aminocarbonyl)-pyrrolidinyl,
with $(C_1-C_4)$alkylthiol or $HNR^8R^9$ wherein $R^8$ and $R^9$ are as defined in formula I, in an inert organic solvent.

With this method it is thus possible to prepare di-substituted derivatives of factors $C_{2a}$ or $D_2$ wherein W and $W^1$ are as defined in formula I, by starting from the corresponding W-substituted compounds, or mono-substituted derivatives of factors $C_{2a}$, $D_2$ or E, wherein $W^1$ is as defined in formula I and W is 2-(aminocarbonyl)-pyrrolidinyl.

The —OG leaving group can be any suitable leaving group known in the art, which can be substituted with the desired thio or aminic moiety under the reaction conditions. Examples of said leaving groups are tosylate, brosylate, nosylate, mesylate, triflate, nonaflate and tresylate; preferred are tosylate and mesylate.

Suitable inert organic solvents are those which do not unfavourably interfere with the reaction course and are capable of at least partially solubilizing the antibiotic starting material. Preferred examples of such solvents are dimethylformamide, dimethylsulfoxide, acetonitrile, tetrahydrofurane, dioxane, hexamethyl-phosphoramide, dichloromethylene and mixtures thereof. Preferably dimethylformamide is employed.

The reaction temperature will vary considerably depending on the specific starting materials and reaction conditions. In general, it is preferred to conduct the reaction at temperatures of from 15° C. to 30° C., conveniently at room temperature.

Also the reaction time varies considerably depending on the other reaction parameters; in general the condensation is completed in about 8 to 24 hours.

Generally, the reaction course is monitored by TLC or preferably by HPLC according to methods known in the art. On the basis of the results of these assays a man skilled in the art will be able to evaluate the reaction course and decide when to stop the reaction and start working up the reaction mass according to known per se techniques, which include, as above, extraction with solvents, precipitation by pH modification, precipitation by addition of non-solvents, etc., in conjunction with further chromatographic separations and purifications techniques, such as flash chromatography (e.g. on silica gel using dichloromethane/methanol mixtures as eluent), reverse phase chromatography or chromatography on neutral aluminium oxide (using dichloromethane/methanol mixtures as eluent).

The starting material of formula X may be prepared according to known per se techniques, by reacting the corresponding compound of formula X wherein the —OG group is hydroxy with a suitable anhydride or chloride containing the —G leaving group, in an inert organic solvent under basic conditions.

Inert organic solvents for preparing the above starting material are those organic solvents which are inert under the conditions of the specific reaction step, do not unfavorably interfere with the reaction course and are capable of at least partially solubilizing the antibiotic material. Examples of said inert organic solvents are dichloromethylene, tetrahydrofurane, dioxane and mixtures thereof; preferably dichloromethylene is employed.

The basic conditions are obtained by adding to the reaction mixture a tertiary aliphatic or alicyclic amine, such as trimethylamine, triethylamine, diisopropylethylamine, N-methylpyrrolidine, N-methyl-morpholine, or heterocyclic bases such as pyridine, picoline and the like; preferably diisopropylethylamine is employed.

The following table lists the structural formula of some representative compounds of the invention, for which antimicrobial activity and preparation methodology are given in the following of the specification. The antibiotic molecule core is antibiotic GE2270 factor $D_2$ (i.e., in the group GE $X^1$ is methyl, $X^2$ is a —$CH_2$—$W^1$ moiety and $X^3$ is methylamino). All the compounds are intented as chirally pure with the same chirality of the natural compound.

| Compound No. | Substituent W | Substituent $W^1$ |
|---|---|---|
| 1 | [structure: O=C(NH—)—pyrrolidinyl-N-CH3] | —$N(C_2H_5)_2$ |
| 2 | " | —$N(CH_3)_2$ |
| 3 | " | —$N(CH_3)$—$(CH_2)_2$—$N(CH_3)_2$ |
| 4 | " | —S—$(CH_2)(CH_3)$ |
| 5 | [structure: O=C(NH—$(CH_2)_2$—$N(C_2H_5)_2$)—pyrrolidinyl-N-CH3] | —OH |
| 6 | [structure: O=C(NH—$(CH_2)_2$—$N(C_2H_5)_2$)—pyrrolidinyl-N-CH3] | —$N(CH_3)_2$ |

The antimicrobial activity of the compounds of the invention can be demonstrated by a series of standard tests in vitro.

The minimal inhibitory concentration (MIC) has been determined by microboth dilution methodology, in the presence of 0.01% (w/v) of bovine serum albumin (BSA). BSA is added to the diluent to avoid possible adherence of the compounds of the invention to the plastic surface of the microtiter wells, as disclosed also by B. Goldstein et al., Antimicrobial Agents and Chemotherapy, 37 (1993), 741–745.

Staphylococci, E. faecalis, E. coli, P. vulgaris, K. pneumoniae and P. aeruginosa were grown in Iso-sensitest broth (Oxoid); Streptococci in Todd Hewitt broth (Difco); H. influenzae in Brain hearth broth (Difco) with 1% of Difco-Supplement C; N. gonorrhoeae in GC Base broth (Difco) supplemented with 1% BBL Isovitalex and anaerobes in Difco Wilkins and Chalgren broth.

All organisms were cultured at 35° C. in air, except H. influenzae and N. gonorrhoeae which were incubated in a 5% $CO_2$ atmosphere and anaerobes which were grown in an anaerobic gas mixture $N_2$—$CO_2$—$H_2$ (80:10:10).

MICs were read after 18–24 h, except for anaerobes, N. gonorrhoeae and H. influenzae (48 h).

Inocula were about $10^4$ cfu/ml for compounds 1, 2, 3 and 4, except for anaerobes (about $10^5$ cfu/ml). For compounds 5, 6 and 7, inocula were about $5 \times 10^5$ cfu/ml.

MICs for some microorganisms are reported below in Table I.

TABLE 1

| Int. code | Strains | MIC of the compounds (µg/ml) | | | | | |
|---|---|---|---|---|---|---|---|
| | | 1 | 2 | 3 | 4 | 5 | 6 |
| 165 | Staph. aureus Tour | 0.13 | 0.13 | 1 | 0.13 | 0.06 | 0.13 |
| 165 | Staph. aureus Tour 10⁶ cfu/ml | 0.25 | 0.13 | 4 | n.t. | 0.13 | n.t. |
| 165 | Staph. aureus Tour 30% b.s. | 0.5 | 0.13 | 1 | n.t. | 0.25 | n.t. |
| 819 | Staph. aureus Smith | 0.13 | 0.13 | 1 | 0.25 | 0.13 | 0.13 |
| 147 | Staph. epidermidis ATCC 12228 | n.t. | 0.13 | 8 | 4 | 0.13 | 0.5 |
| 602 | Staph. haemolyticus clin. is. | 0.13 | 0.25 | 8 | 8 | 0.13 | 0.5 |
| 49 | Strep. pyogenes C203 | 4 | 0.5 | 2 | 64 | 0.13 | 0.13 |
| 44 | Strep. pneumoniae UC41 | 1 | 0.13 | 1 | 0.5 | 0.13 | 0.13 |
| 149 | Enterococcus faecalis ATCC 6919 | 0.06 | 0.06 | 1 | 0.06 | 0.06 | 0.13 |
| 290 | Clostridium perfringens ISS30543 | 0.13 | 0.06 | 4 | 0.016 | 0.06 | 0.06 |
| 1014 | Propionibacterium acnes ATCC6919 | 0.03 | 0.06 | 0.5 | 0.004 | 0.03 | 16 |
| 1011 | Bacteroides fragilis ATCC 25285 | 64 | 128 | >128 | >128 | 32 | 64 |
| 997 | Neisseria gonorrhoeae ISM 68/126 | >128 | 4 | >128 | >128 | 32 | 16 |
| 970 | Haemophilus influenzae type b ATCC19418 | >128 | 8 | >128 | >128 | 8 | >128 |
| 47 | Escherichia coli SKF 12140 | >128 | >128 | >128 | >128 | >128 | >128 |
| 4 | Pseudomonas aeruginosa ATCC10145 | >128 | >128 | >128 | >128 | >128 | >128 |
| 79 | Proteus vulgaris X19H ATCC881 | >128 | >128 | >128 | >128 | >128 | >128 |
| 142 | Klebsiella pneumoniae ISM | >128 | >128 | >128 | >128 | n.t. | >128 | n.t. = not tested

In view of their properties, the compounds of the invention can be used as active ingredients in the preparation of medicaments for human or animal treatment.

In particular, the derivatives of antibiotic GE 2270 of formula I are antimicrobial agents mainly active against gram positive bacteria.

The main therapeutic indication of the antibiotic substances of the invention is thus in the treatment of infections related to the presence of microorganisms susceptible to them.

The term "treatment" is intended to encompass also prophylaxis, therapy and cure.

The patient receiving this treatment is any animal in need, including primates, in particular humans, and other mammals such as equines, cattle, swine, sheep, poultry and pets in general.

The compounds of the invention can be administered as such or in admixture with pharmaceutically acceptable carriers and can also be administered in conjunction with other antimicrobial agents. Conjunctive therapy, thus includes sequential, simultaneous and separate administration of the active compounds in a way that the therapeutical effects of the first administered one is not entirely disappeared when the subsequent is administered.

The dosage of the active ingredient depends on many factors which include type, age and conditions of the patient, specific active ingredient and formulation selected for administration, administration schedule, etc.

Experimental tests for determining the sensitivity of the microorganisms isolated from the patient may also offer useful indication to select the appropriate dosage.

In general, effective antimicrobial dosages are employed per single unit dosage form.

Repeated applications of these dosage forms, e.g. from 2 to 6 times a day, are in general preferred. An effective dosage may be in general in the range 0.5–50 mg/kg body weight/day.

Anyway, the prescribing physician will be able to determine the optimal dosage for a given patient in a given situation.

The compounds of the invention can be formulated into formulation suitable for parenteral administration containing a liquid vehicle, according to procedures known per se in the art. Examples of suitable vehicles for preparing injectable dosage forms of the compounds of the invention are water, aqueous vehicles (e.g. Dextrose injections), water miscible solvents (e.g. ethyl alcohol, polyethylene glycol, propylene glycol, etc.) and non-aqueous vehicles (e.g. "fixed oils" such as corn oil, cottonseed oil, peanut oil and sesame oil). Optionally, the injectable preparation may further contain surface-active agent (e.g. polyoxyethylene sorbitan monooleate or polyethoxylated castor oil), buffers for stabilizing the solution (e.g. citrates, acetates and phosphates) and/or antioxidants (e.g. ascorbic acid or sodium bisulfite).

For instance, a typical formulation for parenteral administration may contain from 5 to 50 mg of a compound of the invention for ml of final preparation. The compound will generally be formulated in water for injection, optionally in admixture with 10–20% of a surface-active agent which may be a polyoxyethylene sorbitan fatty acid ester, a polyoxyethylene castor oil derivative or a polyoxyethylene hydrogenated castor oil derivative and 0–20%; optionally, the formulation may further contain 10–20% of a solubilizing agent such as propylene glycol, dimethylacetamide, dimethylformamide, ter-butyl-N-hydroxycarmabate, 1,2-, 1,3-, or 1,4-butandiol, ethyl oleate, tetrahydrofurfuryl-polyethylene-glycol 200, dimethyl isosorbide, benzyl alcohol and the like. A preferred solubilizing agent is propylene glycol.

Polyoxyethylene sorbitan fatty acid esters are commercially available and some of them are traded under the trade name "Tween". They are also known with the non-proprietary name of "polysorbates". Examples of them are polysorbate 20, 21, 40, 60, 61, 65, 80, 81 and 85. Preferred for use in the formulations of the invention is polysorbate 80 (sorbitan mono-9-octadecenoate, poly(oxy-1,2-ethanediyl) derivatives).

Polyoxyethylene castor oils and polyoxyethylene hydrogenated castor oils are also commercially available. Some of them are traded with the trade name "Cremophor". Examples of such compounds are those known as Cremophor EL (polyethoxylated castor oil), Cremophor RH 40 (polyethoxylated hydrogenated castor oil), Cremophor RH 60 (PEG 60 hydrogenated castor oil) or Emulphor EL-719 (polyoxyethylated vegetable oil).

If necessary, the pH of the preparation may be adjusted with a suitable buffering agent; conveniently, TRIS (i.e.trihydroxymethylaminomethane), phosphate or acetate buffers can be used.

A particularly preferred formulation for parenteral administration is one containing the compound of the invention in the salified form dissolved in distilled water, without any excipients, such as the following:

| | |
|---|---|
| Compound 5 | 50 mg |
| Water for injection | 1 ml |
| pH 5 with acetic acid | |

Care should be taken to set the pH at a value of about 5 for helping the solubilization of the product, but not lower than 4.5 because possible hydrolysis of the oxazoline ring of the molecule may occur.

Examples of formulations of the compounds of the invention in admixture with suitable excipients, for parenteral administration, are the following:

| | | |
|---|---|---|
| A) | compound 5 | 100 mg |
| | propylene glycol | 1 ml |
| | water for injection q.s. | 5 ml |
| | phosphate buffer pH 8–8.5 | |
| B) | compound 5 | 50 mg |
| | Cremophor RH 40 | 1 g |
| | water for injection q.s. | 10 ml |
| | phosphate buffer pH 8–8.5 | |

A further pharmaceutical formulation is represented by a formulation suitable for a topical application on an intact or damaged skin or mucous membrane. Examples of such formulations are powders, ointments, creams and lotions. The excipients in these formulations are the usual pharmaceutically acceptable vehicles such oleaginous ointment bases (e.g. cetyl esters wax, oleic acid, olive oil, paraffin, spermaceti, starch glycerite); absorbent ointment bases (e.g. anhydrous lanolin, hydrophilic petrolatum), emulsion ointment bases (e.g. cetyl alcohol, glyceryl monostearate, lanolin, stearic acid), water-soluble ointment bases (e.g. glycol ethers and their derivatives which include polyethylene glycols, poly(oxy-1,2-ethan ediyl)-alpha-hydro-omega-hydroxy-octadecanoate, polysorbates, and polyethylene glycols mono-stearates).

These formulations may contain other known excipients, such as preservatives and are prepared as known in the art and reported in reference handbooks such as Remington's Pharmaceutical Sciences, Seventeenth edition, 1985, Mack Publishing Co.

A preferred topic preparation is an ointment containing from 1% to 10% of a compound of the present invention.

Besides their use as medicaments in human and veterinary therapy, the compounds of the invention can also be used as animal growth promoters. For this purpose, a compound of the invention is administered orally in a suitable feed. The exact concentration employed is that which is required to provide for the active agent in a growth promotant effective amount when normal amounts of feed are consumed.

The addition of the active compound of the invention to animal feed is preferably accomplished by preparing an appropriate feed premix containing the active compound in an effective amount and incorporating the premix into the complete ration. Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., S. Francisco, USA, 1969 or "Livestock Feeds and Feeding" O and B books, Corvallis, Oreg., USA, 1977).

For better illustrating the invention, the following examples are given.

EXAMPLES

METHOD A—Reaction of starting material GE I (see preparation no. 1) with the selected L- serinamide (see preparation no. 10) and subsequent cyclization Example A1: Preparation of Compound No. 6

DPPA (2.65 mmol) is added to a stirred solution of starting material GE I (1 mmol) and TEA (8 mmol) in DMF (6 ml) at room temperature. After 2 hours the formation of the acylazido reaction product is completed and the hydrochloride salt of L-serinamide (1.6 mmol) and TEA (3.5 mmol) are added. Stirring is continued at room temperature for 2 hours and then the reaction mixture is poured in ice-cold water (90 ml) and the pH of the solution is broght to 10 by addition of 0.1M NaOH. The resulting solid is filtered and allowed to dry in air. Purification by flash chromatography on silica gel 60 (400–230 mesh) with 10% methanol in $CH_2Cl_2$ containing 0.5% TEA yields the condensation product as a white powder.

Methoxycarbonylsulfamoyltriethylammonium hydroxide, inner salt (Burgess reagent) (2.45 mmol) is added under nitrogen atmosphere to a stirred solution of the above prepared condensation product (1 mmol) in dry $CH_2Cl_2$ (30 ml) and dry THF (160 ml) at room temperature. The disappearance of the condensation product starting material and the formation of a more hydrophilic adduct is monitored by HPLC and after 1.5 hours isopropanol (30 ml) is added to quench the excess of reagent. The reaction mixture is thus refluxed for 4 hours and then stirred at room temperature overnight. $Et_2O$ (500 ml) is added and the solid that formed is filtered. Purification by flash chromatography on silica gel 60 (400–230 mesh) with 10% methanol in $CH_2Cl_2$ containing 0.5% TEA followed by a second chromatography on basic aluminum oxide with 5% methanolic $CH_2Cl_2$ yields compound no. 6 as a white solid.

METHOD B—Reaction of starting material GE VI (see preparation no. 7) with the selected L- serinamide (see preparation no. 10)

Example B1: Preparation of Compound No. 5

The hydrochloride salt of L-serinamide (2 mmol) is added to a stirred solution of starting material GE VI (1 mmol) and TEA(2 mmol) in absolute ethanol (35 ml) and $CH_2Cl_2$ (3.5 ml) at room temperature. After 48 hours, solvent is evaporated to a small volume under reduced pressure and the reaction mixture is poured into 1M $NaHCO_3$ (85 ml). The solid that formed is filtered, re-dissolved in 5% methanol in $CH_2Cl_2$, dried over $MgSO_4$ and the solvent evaporated to dryness under reduced pressure. Purification by flash chromatography on silica gel 60 (400–230 mesh) with 10% methanol in $CH_2Cl_2$ containing 1% TEA yields compound no. 5 as a white powder.

METHOD D—Reaction of starting material GE VII (see preparation no. 8) or starting material GE VIIII (see preparation no. 9) with the selected thiol or amine Example D1: Preparation of Compound No. 1

N,N-diethylamine (1.5 mmol) is added to a stirred solution of starting material GE VII (1 mmol) and N,N-diisopropylethylamine (1.5 mmol) in DMF (30 ml) at room temperature. After 24 hours the reaction mixture is poured into water (150 ml) and the solid that formed is filtered off. Purification by flash chromatography on silica gel 60

(400–230 mesh) with 10% methanol in CH$_2$Cl$_2$ yields compound no. 1 as a white powder.

Example D2: Preparation of Compound No. 2

Freshly prepared starting material GE VII, obtained from GE2270 factor D$_2$ (1 mmol) according to preparation no. 8, is dissolved in DMF (10 ml). To this stirred solution, a 33% ethanolic solution of N,N-dimethylamine (1.5 mmol) is added at room temperature. Stirring is continued overnight and the reaction mixture is poured in ice-cold 5% NaHCO$_3$ (100 ml). The solid that formed is filtered, washed over the filter with additional water (35 ml), re- dissolved in 10% methanol in CH$_2$Cl$_2$ (35 ml), dryed over MgSO$_4$ and the solvent is evaporated to a small volume. Addition of Et$_2$O induced precipitation of a solid that is filtered and allowed to dry in air. Preparative HPLC isocratic chromatography [column: Hibar (LiChrosorb RP-18 7 μm) 250×25 mm (Merck); phase: CH$_3$COONa buffer pH 5 (60%), CH$_3$CN (20%), THF (20%); flow: 20 ml/min] yields compound no.2 as an off-white powder.

Example D3: Preparation of Compound No. 3

The reaction is carried out as reported in example D1, but using N,N,N'-trimethylethylenediamine as amine nucleophile.

Purification on silica gel TLC plates with 8% methanol in CH$_2$Cl$_2$ containing 1% TEA yields compound no. 3 as a white powder.

Example D4: Preparation of Compound No. 4

Freshly prepared starting material GE VII, obtained from GE2270 factor D$_2$ (1 mmol) according to preparation no. 8, is dissolved in DMF (25 ml). To this stirred solution, EtSH (4 mmol) is added at room temperature. After 24 hours the reaction mixture is poured into ice-cold water (125 ml) and the solid that formed is filtered off and allowed to air dry. Purification by flash chromatography on silica gel 60 (400–230 mesh) with 7% methanol in CH$_2$Cl$_2$ yields compound no. 4 as a white powder.

Example D5: Preparation of Compound No. 6

Freshly prepared starting material GE VIII, obtained from compound no. 5 (1 mmol) according to preparation no. 9, is dissolved in DMF (20 ml). To this stirred solution, a 33% ethanolic solution of N,N-dimethylamine (1.5 mmol) is added at room temperature. Stirring is continued overnight and the reaction mixture is poured in ice-cold 5% NaHCO$_3$ (100 ml). The solid that formed is filtered off, allowed to air dry and purified on neutral aluminum oxide with 5% methanol in CH$_2$Cl$_2$. Compound no.6 is obtained as a white powder.

The compounds obtained according to the above examples have been characterized by their HPLC retention times, according to the following methodology;

Column: RP18 (Merck) 5 μm

Eluent: Phase A: 0.05M ammonium formate buffer
Phase B: acetonitrile

Gradient: minutes 0 5 20 30 31 35
% of B 40 40 80 80 85 85

Flow rate: 0.7 ml/min

Detection: UV at 254 nm

| Compound | Retention Time |
|---|---|
| 1 | 16.1 |
| 2 | 13.0 |
| 3 | 14.1 |
| 4 | 16.4 |
| 5 | 17.8 |
| 6 | 20.2 |

Compounds have also been characterized by means of $^1$H-NMR spectra and Fab-MS spectra; methodologies and data are reported hereinafter.

The $^1$H-NMR spectra are recorded with a Bruker AM500 or AMX 600 spectrometer using DMSO-d$_6$ (hexadeuterodimethylsulfoxide) as solvent. (br=broad, s=singlet, d=doublet, dd=doublet of doublets, t=triplet, q=quartet, m=multiplet).

Compound 1

$^1$H-NMR (DMSOd$_6$) δ(ppm): 0.84(d, 3H); 0.88(d, 3H); 0.98(t, 6H); 1.35(br d, 1H); 2.02–1.82(m, 3H); 2.15(m, 2H); 2.48(d, 3H); 2.55(m, 4H); 2.59(s, 3H); 2.71(dd, 1H); 3.82 (m, 2H); 3.98(dd, 1H); 4.09(dd, 2H); 4.25(m, 2H); 4.57(dd, 1H); 4.81(dd, 1H); 5.00(dd, 1H); 5.14(dd,1H); 5.24(m, 2H); 5.31(m, 1H); 6.00(d, 1H); 6.94(s, 1H); 7.45–7.20(m, 8H); 8.29(m, 2H); 8.42(m, 2H); 8.54(s, 1H); 8.60(s, 1H); 8.68(m, 2H); 8.99(d, 1H).

Compound 2

$^1$H-NMR (DMSOd$_6$) δ(ppm): 0.84(d, 3H); 0.88(d, 3H); 1.35(br d, 1H); 2.00–1.82(m, 3H); 2.15(m, 2H); 2.24(s, 6H); 2.47(d, 3H); 2.59(s, 3H); 2.71(dd, 1H); 3.82(m, 2H); 3.95 (dd, 1H); 4.02(dd, 2H); 4.25(m, 2H); 4.56(dd, 1H); 4.81(dd, 1H); 5.01(d, 1H); 5.16(dd, 1H); 5.23(m, 2H); 5.30(dd, 1H); 6.94(s, 1H); 7.45–7.21(m, 8H); 8.29(m, 2H); 8.42(m, 2H); 8.54(s, 1H); 8.60(s, 1H); 8.68(m, 2H); 9.05(br d, 1H).

Compound 3

$^1$H-NMR (DMSOd$_6$) δ(ppm): 0.84(d, 3H); 0.88(d, 3H); 1.39(br d, 1H); 2.00–1.85(m, 3H); 2.15(s, 8H); 2.25(s, 3H); 2.40(m, 2H); 2.47(d, 3H); 2.59(s, 3H); 2.64(m, 2H); 2.71 (dd, 1H); 3.79(m, 2H); 3.98(dd, 1H); 4.11(s, 2H); 4.26(m, 2H); 4.57(dd, 1H); 4.81(dd, 1H); 5.01(m, 1H); 5.16(dd, 1H); 5.24(m, 2H); 5.30(m, 1H); 6.02(s, 1H); 6.94(s, 1H); 7.38–7.20(m, 7H); 7.41(m, 1H); 8.28(d, 1H); 8.30(s, 1H); 8.42(d, 1H); 8.46(m, 1H); 8.54(s, 1H); 8.60(s, 1H); 8.67(d, 1H); 8.70(d, 1H); 9.00(d, 1H).

Compound 4

$^1$H-NMR (DMSOd$_6$) δ(ppm): 0.85(d, 3H); 0.88(d, 3H); 1.15(t, 3H); 1.37(br d, 1H); 2.00–1.85(m, 3H); 2.16(m, 2H); 2.47(d, 3H); 2.59(s, 3H); 2.71(dd, 1H); 3.52–3.20(m, 2H); 3.81(m, 2H); 3.97(dd, 1H); 4.25(m, 2H); 4.46[q(ab), 2H]; 4.57(dd, 1H); 4.81(dd, 1H); 5.02(dd, 1H); 5.19(dd, 1H); 5.23(m, 2H); 5.30(dd, 1H); 6.02(d, 1H); 6.94(s, 1H); 7.42–7.20(m, 8H); 8.28(d, 1H); 8.29(s, 1H); 8.42(d, 1H); 8.45(m, 1H); 8.54(s, 1H); 8.60(s, 1H); 8.63(d, 1H); 8.70(d, 1H); 8.99(d, 1H).

Compound 5

$^1$H-NMR (DMSOd$_6$) δ(ppm): 0.85(d, 3H); 0.89(d, 3H); 1.01(br s, 6H); 1.32(br d, 1H); 1.87(m, 1H); 1.96(m, 1H); 2.16(m, 3H); 2.48(d, 3H); 2.59(s, 3H); 2.72(dd, 1H); 2.85–2.30(m, 4H); 3.60–3.05(m, 4H); 3.90–3.75(m, 2H);

4.00(dd, 1H); 4.28(m, 2H); 4.57(dd, 1H); 4.80(dd, 1H); 4.98(m, 3H); 5.18(dd, 1H); 5.24(m, 2H); 5.30(dd, 1H); 5.97(t, 1H); 6.02(d, 1H); 7.50–7.20(m, 7H); 7.82(br s, 1H); 8.28(d, 1H); 8.29(s, 1H); 8.36(dd, 1H); 8.42(d, 1H); 8.54(s, 1H); 8.60(s, 1H); 8.68(d, 2H); 9.01(d, 1H).

Compound 6

$^1$H-NMR (DMSOd$_6$) δ(ppm): 0.85(d, 3H); 0.89(d, 3H); 0.98(m, 6H); 1.42(br d, 1H); 1.88(m, 1H); 1.97(m, 1H); 2.14(m, 3H); 2.24(s, 6H); 2.48(d, 3H); 2.59(s, 3H); 2.65–2.33(m, 4H); 2.71(d, 1H); 3.42–3.05(m, 4H); 3.82(m, 2H); 4.02(m, 3H); 4.28(m, 2H); 4.58(dd, 1H); 4.80(dd, 1H); 5.03(dd, 1H); 5.17(dd, 1H); 5.25(m, 2H); 5.29(dd, 1H); 5.98(d, 1H); 7.41–7.20(m, 7H); 7.75(br s, 1H); 8.28(m, 2H); 8.42(m, 2H); 8.52(s, 1H); 8.58(s, 1H); 8.65(d, 1H); 8.69(d, 1H); 8.95(d, 1H).

The FAB-MS spectra are obtained with a triple stage quadrupole spectrometer TSQ 700 Finningan:

Compound 1 FAB-MS m/z 1331 (MH$^+$, 100%)
Compound 2 FAB-MS m/z 1303 (MH$^+$, 100%)
Compound 3 FAB-MS m/z 1360 (MH$^+$, 100%)
Compound 4 FAB-MS m/z 1320 (MH$^+$, 100%)
Compound 5 FAB-MS m/z 1375 (MH$^+$, 100%)
Compound 6 FAB-MS m/z 1388 (MH$^+$, 100%).

PREPARATION OF STARTING MATERIALS

PREPARATION OF ANTIBIOTIC GE2270 STARTING MATERIALS

Preparation No. 1: Starting Material GE I

Compound no. 2 (see example D2)(1 mmol) in THF (8 ml) and water (5 ml) is stirred at 60° C. in the presence of 30% H$_2$SO$_4$ (0.37 ml). After 3 hours the reaction mixture is cooled to room temperature and the pH of the solution is brought to 12 by addition of 30% NaOH. Stirring is continued for additional 1 hour at room temperature, then the pH of the solution is adjusted to 5 by addition of 1M H$_2$SO$_4$ and the reaction mass is poured into water. The solid that precipitated is filtered, washed over the filter with more water and then allowed to air dry to yield starting material GE I as a white powder.

Preparation 2: GE2270 Factor D$_2$

GE2270 factor D$_2$ is prepared by fermentation of *Planobispora rosea* ATCC 53773 as described in European Patent Application Publication no.451486 which has as its equivalent, U.S. Pat. No. 5,747,295, which is hereby incorporated by reference. Recovery and isolation of the factor are as described therein.

Preparation 3: Starting Material GE II

Starting material GE II is prepared by controlled acid hydrolysis from GE2270 factor D$_2$ as described in European Patent Application Publication no.565567 which has as its equivalent, U.S. Pat. No. 5,599,791, which is hereby incorporated by reference.

Preparation 4: Starting Material GE III

Starting material GE II (1 mmol) is suspended in ice-cold 13% methanolic ammonia (30 ml) with stirring in a stoppered flask. The temperature is allowed to raise to room temperature and the starting material went in solution. Stirring is continued overnight at this temperature and thus the solvent is removed under reduced pressure. The solid obtained is then triturated with Et$_2$O (30 ml), filtered and purified by flash chromatography on silica gel 60 (400–230 mesh) with 7% methanol in CH$_2$Cl$_2$. Starting material GE III is obtained as a white powder.

Preparation 5: Starting Material GE IV

N,N-dimethylaminopyridine (0.1 mmol) and acetic anhydride (2.5 mmol) are added to a stirred solution of starting material GE III (1 mmol) in dry CH$_2$Cl$_2$ (35 ml) and pyridine (3.5 ml) at room temperature. After 4 hours, the solvent is evaporated to dryness under reduced pressure and Et$_2$O (35 ml) is added to precipitate a solid that is filtered, washed with additional Et$_2$O (20 ml) and allowed to air dry to yield starting material GE IV as a white solid.

Preparation 6: Starting Material GE V

A solution of Burgess reagent (3.5 mmol) in dry CH$_2$Cl$_2$ (3 ml) is added dropwise to a stirred solution of starting material GE IV (1 mmol) in dry CH$_2$Cl$_2$ (15 ml) and TEA (1.5 mmol) at room temperature. Stirring is continued overnight at this temperature, thus the reaction mixture is concentrated to a small volume under reduced pressure. Addition of Et$_2$O (35 ml) produced the precipitation of a solid which is used as such in the next step.

The solid from the previous step is dissolved in dioxane (22 ml) and 1M NaOH (8.8 ml) is added portion-wise over 24 hours at room temperature with stirring. After additional 12 hours, removal of both acetyls is completed and the reaction mass is poured in water (100 ml). The solid that precipiteted is collected by centrifugation, dissolved in absolute ethanol (100 ml) and the solvent evaporated under reduced pressure to yield a solid that is purified by flash chromatography on silica gel 60 (400–230 mesh) with 4% methanol in CH$_2$Cl$_2$. Starting material GE V is obtained as a white powder.

Preparation 7: Starting Material GE VI

Anhydrous HCl gas is bubbled through a well stirred solution of starting material GE V (1 mmol) in CHCl$_3$ (50 ml) and absolute ethanol (50 ml) cooled at 0° C. by an ice-bath. After 2 hours bubbling of HCl gas is interrupted, the flask is stoppered and stored overnight in a fridge at 4° C . The reaction mixture is then concentrated to a small volume under reduced pressure and carefully poured in a saturated solution of Na$_2$CO$_3$ (100 ml) cooled at 0° C. The solid that formed is recovered by centrifugation, re-suspended in water (50 ml), filtered and washed over the filter with water (2×20 ml) to yield starting material GE VI as a white solid.

Preparation 8: Starting Material GE VII

A solution of p-toluensulfonic anhydride (3 mmol) in dry CH$_2$Cl$_2$ (20 ml) is added to a well stirred suspension of GE2270 factor D$_2$ (1 mmol) and N,N-dimethylaminopyridine (0.1 mmol) in CH$_2$Cl$_2$ (20 ml) and N,N-diisopropylethylamine (4 ml) at room temperature. With time, the reaction mixture turned clear and after 5 hours the reaction is completed. Solvents are evaporated off under reduced pressure and the residual solid of starting material GE VII is used as such in the next step.

Preparation 9: Starting Material GE VIII p-Toluensulfonic anhydride (3 mmol) is added to a stirred solution of compound 5 (see example B1) (1 mmol) and N,N-dimethylaminopyridine (0.1 mmol) in CH$_2$Cl$_2$ (120 ml) and N,N-diisopropylethylamine (3.5 ml) at room temperature. After 3 hours the reaction is completed and solvents are evaporated off under reduced pressure. The residual solid of starting material GE VIII is used as such in the next step.

PREPARATION OF THE SERINAMIDES STARTING MATERIALS

Preparation 10: Preparation of Serinamide for Compounds 5 and 6.

A mixture of Cbz-L-Proline (Novabiochem) (145.0 g, 0.58 mol) and N- hydroxysuccinimide (Aldrich) (66.9 g, 0.58 mol) in EtOAc (1.8 L) is cooled at −5° C. with stirring under nitrogen atmosphere. To this solution, a solution of DCC (132.1 g, 0.64 mol) in EtOAc (265 ml) is added over 20 min so to mantain the internal temperature at −5° C. The temperature is then allowed to rise to ambient temperature and stirring is continued for additional 3 hours. Precipitated dicyclohexylurea is filtered off and the filtrate is used as such in the next step.

To the above prepared solution of N-Cbz-L-proline N-hydroxysuccinimide ester, N,N-diethyl-ethylenediamine (Aldrich) (67.6 g, 0.58 mol) is added over 15 min while stirring at room temperature. After 18 hours the solid that had formed is filtered off, washed over the filter with EtOAc (300 ml) and the filtrate is extracted with 1.04M HCl (725 ml). The aqueous extracts are cooled by an ice-bath, the pH is brought to 10 by careful addition of 1M NaOH and then extracted with CH$_2$Cl$_2$ (4×730 ml). The organic extracts are combined, dried (MgSO$_4$) and the solvent evaporated to dryness under reduced pressure to provide an oil which is diluted with Et$_2$O (60 ml) and hexane (2 L) under stirring. After 18 hours at room temperature and 1 hour in an ice-bath, the solid product is filtered off, washed with an ice-cold 9:1 mixture of hexane/Et$_2$O (2×200 ml) and air-dried at ambient temperature to yield N,N-diethylethylene-diamine N-Cbz-L-prolinamide (158.6 g, 79% yield) as a white powder.

10% Pd/C (5 g) is charged to a 1-L 3-necked flask fitted with a magnetic stirrer, thermometer and continuous nitrogen purge. The catalyst is wetted with water (20 ml) and then ammonium formate (13.6 g, 0.22 mol) is added in one portion. The mixture is stirred while adding a solution of the above prepared N,N-diethylethylenediamine N-Cbz-L-prolinamide (50 g, 0.14 mol) in methanol (189 ml) over 20 min. After 30 min the reaction is completed, the catalyst is filtered off, washed over the filter with additional methanol (4×25 ml) and the filtrate is evaporated to dryness under reduced pressure to yield N,N-diethylethylenediamine-L-prolinamide (30.7 g, 100% yield) as an oil.

A mixture of N-Cbz-L-serine (Novabiochem) (100 g, 0.42 mol) and pentafluorophenol (Aldrich) (84.7 g, 0.46 mol) in anhydrous DMF (250 ml) are cooled with stirring under nitrogen to −10° C. To this solution, a solution of DCC (95.0 g, 0.46 mol) in anhydrous DMF (125 ml) is added over 30 min while keeping the reaction temperature at −10° C. The reaction mixture is stirred at −10 to −5° C. for an additional 30 min and then at room temperature for 3 hours. The reaction mixture is poured into water (3.76 L). After stirring for 15 min, the solid that precipitated out is filtered, washed over the filter with water (3×500 ml) and air dried at room temperature. The solid is then taken up in EtOAc (1 L) and the residual solid (mainly dicyclohexylurea) is filtered off and washed with more EtOAc (3×150 ml). The combined EtOAc solutions are evaporated to dryness under reduced pressure. The residual solid is dissolved in hot CH$_2$Cl$_2$ (3.2 L). The hot solution is gravity filtered and the solvent is boiled off until solid began to crystallize. The solid which crystallized is filtered and air dried to ambient temperature to give N-Cbz-L-serine pentafluorophenyl ester (130.8 g, 77% yield) as a white solid.

A solution of N,N-diethylethylenediamine-L-prolinamide (63.1 g, 0.30 mol) in CH$_2$Cl$_2$ (500 ml) is charged to 2-L 3-necked flask fitted with a magnetic stirrer, thermometer and continuous nitrogen purge. The solution is stirred while adding N-Cbz-L-serine pentafluorophenyl ester (121.6 g, 0.30 mol) as a solid over 10 min. The reaction mixture is stirred for an additional 1 hour at room temperature and then is washed with 1N NaOH (105 ml followed by 2×210 ml). The organic phase is separated, dried (MgSO$_4$) and then evaporated to dryness under reduced pressure. The glassy product is diluted with Et$_2$O (200 ml) and the mixture is warmed to 30° C. and solid began to form. After all of the glass had solified, the mixture is diluted with pentane (200 ml). Solid is filtered off, washed with pentane, then air-dried at room temperature to give a solid which is slurried in Et$_2$O (250 ml). Solid is filtered off and allowed to air-dry at room temperature to give the expected N-Cbz-L-serinamide (119.7 g, 92% yield) as a white powder.

Deprotection of the Cbz-protecting group is carried out just before usage of the serinamide.

A suspension of the above prepared N-Cbz-L-serinamide (5.0 g, 11.52 mmol) and 10% palladium on charcoal (500 mg) in methanol (90 ml) is hydrogenated at room temperature and atmospheric pressure in the presence of 20% methanolic HCl (4.5 ml) for 1 hour. The catalyst is filtered off, washed over the filter with methanol (2×100 ml) and the solvent evaporated to dryness under reduced pressure. Trituration of the waxy solid with Et$_2$O yields the expected serinamide hydrochloric salt (4.3 g, 100% yield) as a white powder.

We claim:

1. Derivatives of GE2270 factors C$_{2a}$, D$_2$ and E of general formula I

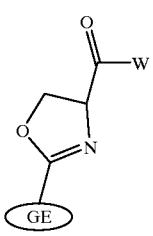

wherein

W represents a 2-(aminocarbonyl)-pyrrolidinyl moiety of formula

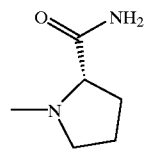

or a group of formula

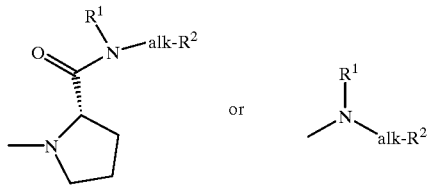

wherein

R¹ represents hydrogen or $(C_1-C_4)$alkyl alk represents $(C_1-C_4)$alkylene

R² represents a NR³R⁴ group wherein R³ and R⁴ independently represent $(C_1-C_4)$alkyl or di$(C_1-C_4)$alkylamino-$(C_1-C_4)$alkylene, or a five or six membered heterocycle ring containing one nitrogen atom and optionally a further heteroatom selected from nitrogen and oxygen, optionally substituted with a group selected from $(C_1-C_4)$alkyl, hydroxy$(C_1-C_4)$alkylene, di$(C_1-C_4)$alkylamino or di$(C_1-C_4)$alkylamino-$(C_1-C_4)$alkylene, or R¹ and alk-R² together with the adjacent nitrogen atom form a five or six membered heterocycle ring optionally containing a further heteroatom selected from oxygen and nitrogen, optionally substituted with a group selected from $(C_1-C_4)$ alkyl, di$(C_1-C_4)$alkylamino, di$(C_1-C_4)$ alkylamino$(C_1-C_4)$alkylene, hydroxy$(C_1-C_4)$ alkylene, and a alk₂-R⁵ group wherein alk₂ is $(C_1-C_4)$alkyl and R⁵ represents a NR⁶R⁷ group wherein R⁶ and R⁷ independently represent $(C_1-C_4)$alkyl or di$(C_1-C_4)$ alkylamino$(C_1-C_4)$alkylene or a five or six membered heterocycle ring containing one or two heteroatoms selected from nitrogen and oxygen, optionally substituted with a group selected from $(C_1-C_4)$alkyl, hydroxy$(C_1-C_4)$alkylene, di$(C_1-C_4)$ alkylamino or di$(C_1-C_4)$alkylamino$(C_1-C_4)$ alkylene;

the group GE represents the antibiotic core portion of formula

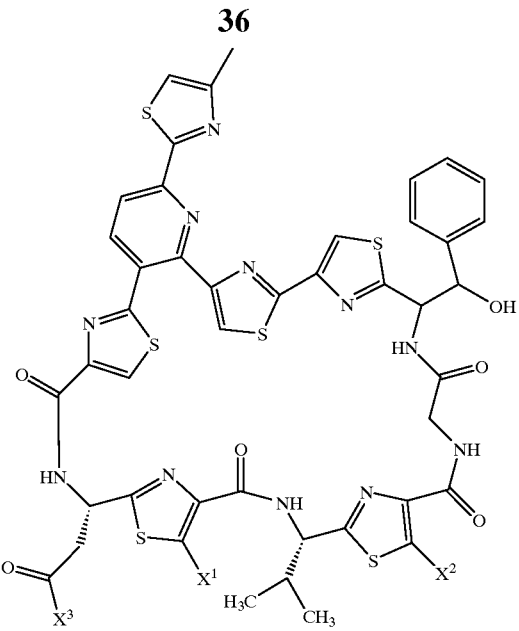

wherein:

X¹ is methyl, X² is a —CH₂—W¹ moiety and X³ is methylamino or amino, or

X¹ is a —CH₂—W¹ moiety, X² is methoxymethylene and X³ is methylamino, wherein W¹ represents hydroxy, $(C_1-C_4)$alkylthio or a group NR⁸R⁹ wherein R⁸ represents $(C_1-C_4)$alkyl, R⁹ $(C_1-C_4)$alkyl or di$(C_1-C_4)$alkylamino-$(C_1-C_4)$ alkylene or R⁸ and R⁹ together with the adjacent nitrogen atom form a five or six membered heterocycle ring optionally containing a further heteroatom selected from oxygen and nitrogen, optionally substituted with a group selected from $(C_1-C_4)$ alkyl, di$(C_1-C_4)$alkylamino, di$(C_1-C_4)$ alkylamino$(C_1-C_4)$alkylene, hydroxy$(C_1-C_4)$ alkylene;

with the proviso that when X³ is amino, then W must be 2-(aminocarbonyl)-pyrrolidinyl;

with the further proviso that when W is 2-(aminocarbonyl)pyrrolidinyl, then W¹ can not be hydroxy;

and the pharmaceutically acceptable salts thereof.

2. Compound according to claim 1 of formula Ia

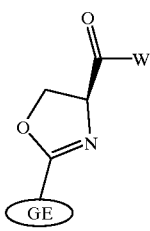

wherein the moieties GE and W are as defined in claim 1.

3. Compound according to claim 1, the moiety W being as defined in formula I or Ia wherein $R^1$ represents hydrogen or $(C_1-C_4)$alkyl, alk represents $(C_1-C_4)$alkylene $R^2$ represents a $NR^3R^4$ group wherein $R^3$ and $R^4$ independently represent $(C_1-C_4)$alkyl or di$(C_1-C_4)$alkylamino-$(C_1-C_4)$alkylene, the moiety GE being as defined in formula I or Ia.

4. Compound according to claim 1, wherein the moiety GE is as defined in formula I or Ia, $X^1$, $X^2$ and $X^3$ being as defined, wherein $W^1$ represents hydroxy, $(C_1-C_4)$alkylthio or a group $NR^8R^9$ wherein $R^8$ is $(C_1-C_4)$alkyl, and $R^9$ is $(C_1-C_4)$alkyl or di$(C_1-C_4)$alkylamino-$(C_1-C_4)$alkylene, the moiety W being as defined.

5. Compound according to claim 1, wherein the W represents a moiety of formula

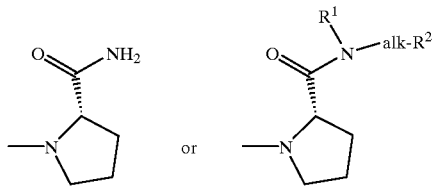

$R^1$ and $R^2$ being as defined.

6. Process for preparing a compound of claim 1, which comprises:

a) reacting a compound of formula III

III wherein the group GE is as defined in formula I, $X^1$ and $X^2$ being as defined and $X^3$ being methylamino, with the proviso that when $W^1$ is hydroxy it must be protected with a suitable protecting group removable under neutral deprotecting conditions, with a suitable serinamide of formula IVa or IVb:

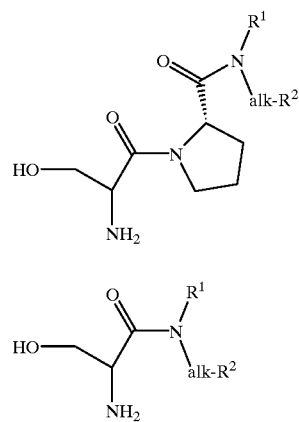

wherein $R^1$, alk and $R^2$ are as in formula I, in an inert aprotic organic solvent in the presence of a condensing agent;

b) cyclizing the serine moiety of the obtained compound of formula IIIa or IIIb:

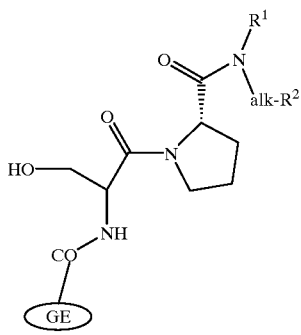

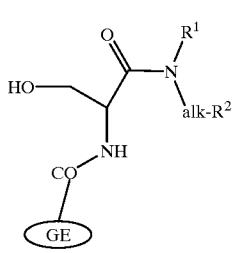

with a suitable cyclizing reactant, in order to obtain the desired oxazoline ring;

c) removing, if present, the protective group of the —OH moiety.

7. Process according to claim 6 wherein a salt-forming base is further added to the reaction mixture of step a).

8. Process according to claim 6 wherein the salt-forming base is a tertiary organic aliphatic or alicyclic amine or heterocyclic base.

9. Process according to claim 6 wherein the inert organic solvent of step a) is selected from organic amides, ethers of glycols and polyols, phosphoramides, sulfoxides and mixtures thereof.

10. Process according to claim 9 wherein the inert organic solvent is selected from dimethylformamide, dimethoxyethane, hexamethylphosphoramide, dimethylsulfoxide, dioxane, and mixtures thereof.

11. Process according to claim 6 wherein the condensing agent is selected from diphenyl-phosphorazidate, diethyl-phosphorazidate, di(4-nitrophenyl)-phosphorazidate, dimorpholyl-phosphorazidate, diphenylphosphorochloridate and benzotriazol-1-yl-oxy-tripyrrolidinophosphoniumhexafluorophosphate.

12. Process according to claim 6 wherein the serine cyclization of step b) is obtained by reacting compound IIIa with methoxycarbonylsulfamoyl-triethylammonium hydroxide, inner salt (Burgess reagent), in an organic aprotic oxygenated solvent and refluxing the reacted mixture.

13. Process according to claim 12 wherein the organic aprotic oxygenated solvent is selected from tetrahydrofuran and dioxane.

14. Process according to claim 12 wherein a chlorinated solvent is further added to the reaction mixture.

15. Process according to claim 12 wherein a salt-forming base is further added to the reaction mixture.

16. Process according to claim 12 wherein a secondary or tertiary $(C_3-C_5)$alcohol is subsequently added to the reaction mixture for quenching the reaction.

17. Process according to claim 6 wherein, when the group $W^1$ of formula I representing hydroxy is protected with nitrobenzyl ether or allyl carbonate, the removal of the protecting group according to step c) is carried out by UV irradiation (at 280–320 nm) or with tetrakis (triphenylphosphine)Pd(O), respectively.

18. Process for preparing a compound of claim 1, which comprises reacting a compound of formula V

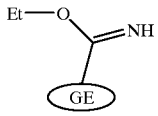

wherein the group GE is as defined in claim 1, with a serinamide, or an acid addition salt thereof, of formula IV:

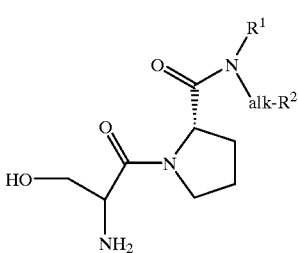

wherein $R^1$, alk and $R^2$ are as in claim 1, in a protic organic solvent.

19. Process according to claim 18 wherein a salt-forming base is further added to the reaction mixture.

20. Process according to claim 19 wherein the salt-forming base is a tertiary organic aliphatic or alicyclic amine or heterocyclic base.

21. Process according to claim 18 wherein the protic organic solvent is selected from methanol, ethanol, propanol, iso-propanol, butanol, iso-butanol and mixtures thereof.

22. Process for preparing a compound of claim 1, which comprises reacting a compound of formula IXa or IXb

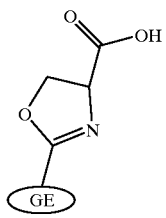

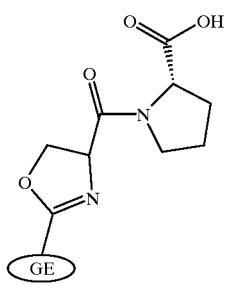

wherein the group GE is as defined in formula I, $X^1$ and $X^2$ being as defined and $X^3$ being methylamino, with an amine of formula VI:

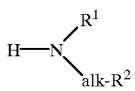

wherein $R^1$, alk, and $R^2$ are as defined in formula I, in the presence of an inert organic solvent and of a condensing agent.

23. Process according to claim 22 wherein, when the compound of formula VI is employed in the salified form, a strong acid is further added to the reaction mixture.

24. Process according to claim 22 wherein a salt-forming base is further added to the reaction mixture.

25. Process according to claim 24 wherein the salt-forming base is a tertiary organic aliphatic or alicyclic amine or heterocyclic base.

26. Process according to claim 22 wherein the inert organic solvent is selected from organic amides, ethers of glycols and polyols, phosphoramides, sulfoxides and mixtures thereof.

27. Process according to claim 22 wherein the inert organic solvent is selected from dimethylformamide, dimethoxyethane, hexamethylphosphoramide, dimethylsulfoxide, dioxane, and mixtures thereof.

28. Process according to claim 22 wherein the condensing agent is selected from diphenyl-phosphor-azidate, diethyl-phosphorazidate, di(4-nitrophenyl)-phosphorazidate, dimorpholyl-phosphorazidate, diphenylphosphorochloridate and benzotriazol-1-yl-oxy-tripyrrolidinophosphoniumhexafluorophosphate.

29. Process for preparing a compound of claim 1, which comprises reacting a compound of formula X

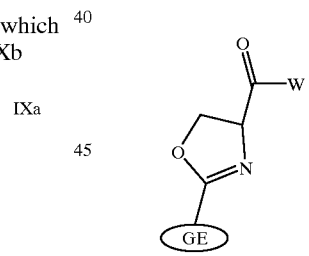

wherein W is as defined in formula I and GE is as defined in formula I, $W^1$ being a suitable leaving group which can be substituted with the desired thio or aminic moiety under the reaction conditions, with the proviso that when GE represents the core portion of GE2270 factor E, then W is 2-(aminocarbonyl)-pyrrolidinyl, with $(C_1–C_4)$alkylthiol or $HNR^8R^9$ wherein $R^8$ and $R^9$ are as defined in formula I, in an inert organic solvent.

30. Process according to claim 29 wherein the leaving group is selected from tosylate, brosylate, nosylate, mesylate, triflate, nonaflate and tresylate.

31. Process according to claim 29 wherein the inert organic solvent is selected from dimethylformamide, dimethylsulfoxide, acetonitrile, tetrahydrofurane, dioxane, hexamethylphosphoramide, dichloromethylene and mixtures thereof.

32. Compound of general formula

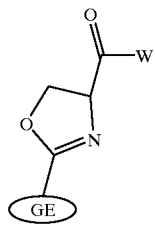

wherein GE is as defined in claim 1 and W represents a group of formula

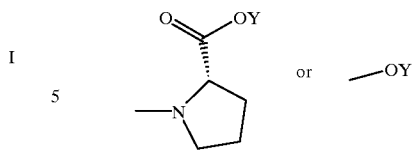

wherein Y represents hydrogen or $(C_1-C_4)$alkyl.

33. Pharmaceutical composition containing a compound of any of claim 1, in admixture with a pharmaceutical acceptable carrier.

34. Method of treating a microbial infection in a patient in need thereof, comprising administering to said patient an effective antimicrobial amount of a compound of claim 1.

* * * * *